US011871993B2

(12) United States Patent
Hall et al.

(10) Patent No.: US 11,871,993 B2
(45) Date of Patent: Jan. 16, 2024

(54) DRY EYE MITIGATION FOR OCULAR ABERROMETRY SYSTEMS AND METHODS

(71) Applicant: Alcon Inc., Fribourg (CH)

(72) Inventors: Max Hall, Irvine, CA (US); Thomas Padrick, Seattle, WA (US); Edwin Jay Sarver, Cookeville, TN (US)

(73) Assignee: Alcon Inc., Fribourg (CH)

( * ) Notice: Subject to any disclaimer, the term of this patent is extended or adjusted under 35 U.S.C. 154(b) by 487 days.

(21) Appl. No.: 17/033,360

(22) Filed: Sep. 25, 2020

(65) Prior Publication Data

US 2021/0093184 A1 Apr. 1, 2021

Related U.S. Application Data

(60) Provisional application No. 62/908,584, filed on Sep. 30, 2019.

(51) Int. Cl.
*A61B 3/10* (2006.01)
*G16H 30/40* (2018.01)
*A61B 3/15* (2006.01)

(52) U.S. Cl.
CPC .............. *A61B 3/101* (2013.01); *A61B 3/102* (2013.01); *A61B 3/152* (2013.01); *G16H 30/40* (2018.01); *A61B 2560/0223* (2013.01)

(58) Field of Classification Search
CPC ......... A61B 3/101; A61B 3/102; A61B 3/152; A61B 2560/0223; G16H 30/40

(Continued)

(56) References Cited

U.S. PATENT DOCUMENTS

2002/0097376 A1* 7/2002 Applegate ............ A61B 3/1015
351/205
2007/0216867 A1* 9/2007 Campbell ........... A61F 9/00806
351/246

(Continued)

FOREIGN PATENT DOCUMENTS

WO 2017019117 A1 2/2017
WO WO-2017019117 A1 * 2/2017 ........... A61B 3/0025

OTHER PUBLICATIONS

Li, et al: "Changes in aberrations and retinal image quality due to tear film dynamics"; Optics Express, OSA Publishing, US; vol. 14, No. 25; Dec. 11, 2006 (Dec. 11, 2006); pp. 12552-12559, XP009524264, ISSN: 1094-4087.

(Continued)

*Primary Examiner* — Sharrief I Broome

(57) ABSTRACT

Techniques are disclosed for systems and methods to provide dry eye and/or tear film hydration monitoring in the context of ocular aberrometry. An ocular aberrometry system includes a wavefront sensor configured to provide wavefront sensor data associated with an optical target monitored by the ocular aberrometry system and a logic device configured to communicate with the wavefront sensor. The logic device is configured to receive ocular aberrometry output data including at least the wavefront sensor data provided by the wavefront sensor, determine a tear film hydration state associated with the optical target based, at least in part, on the received ocular aberrometry output data, and generate user feedback corresponding to the determined tear film hydration state based, at least in part, on the received aberrometry output data and/or the determined tear film hydration state.

22 Claims, 13 Drawing Sheets

(58) Field of Classification Search
USPC .................... 351/221, 220, 222, 233, 223
See application file for complete search history.

(56) References Cited

U.S. PATENT DOCUMENTS

| | | | | |
|---|---|---|---|---|
| 2009/0021696 | A1* | 1/2009 | Chang | A61B 3/14 |
| | | | | 351/221 |
| 2015/0294134 | A1* | 10/2015 | Giannozzi | A61B 3/1015 |
| | | | | 382/128 |
| 2016/0000316 | A1* | 1/2016 | Copland | A61B 3/103 |
| | | | | 351/221 |
| 2016/0000318 | A1* | 1/2016 | Copland | A61B 5/1103 |
| | | | | 351/208 |

OTHER PUBLICATIONS

Shizuka Koh et al: "Simultaneous Measurement of Tear Film Dynamics Using Wavefront Sensor and Optical Coherence Tomography"; Investigative Opthalmology & Visual Science, vol. 51, No. 7, Jul. 1, 2010 (Jul. 1, 2010), p. 3441, XP055753686, ISSN: 1552-5783.

\* cited by examiner

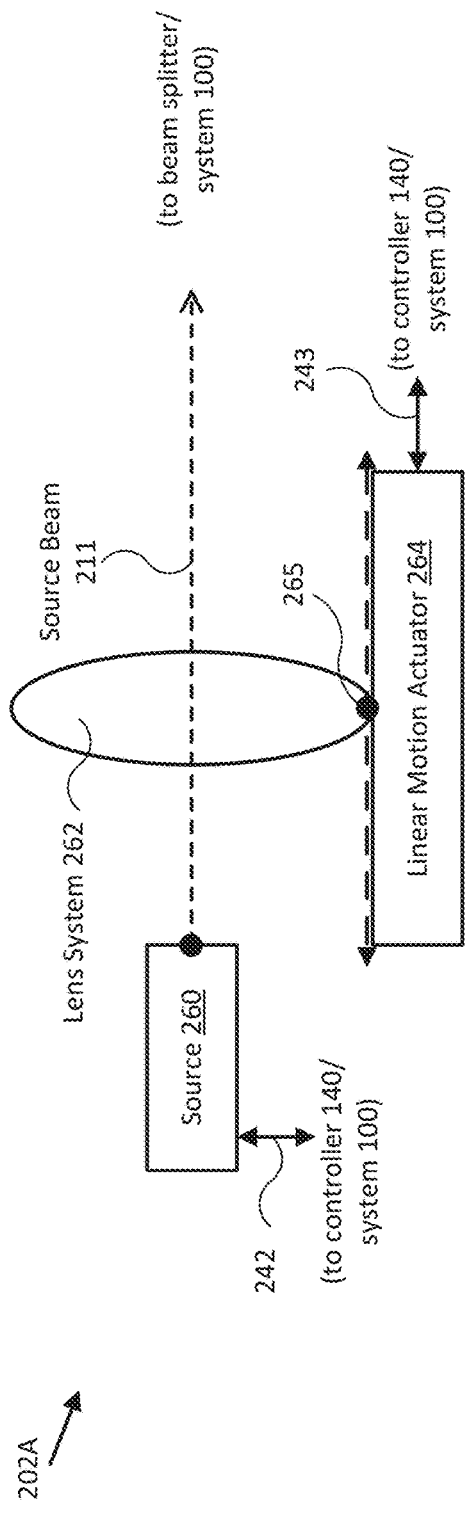
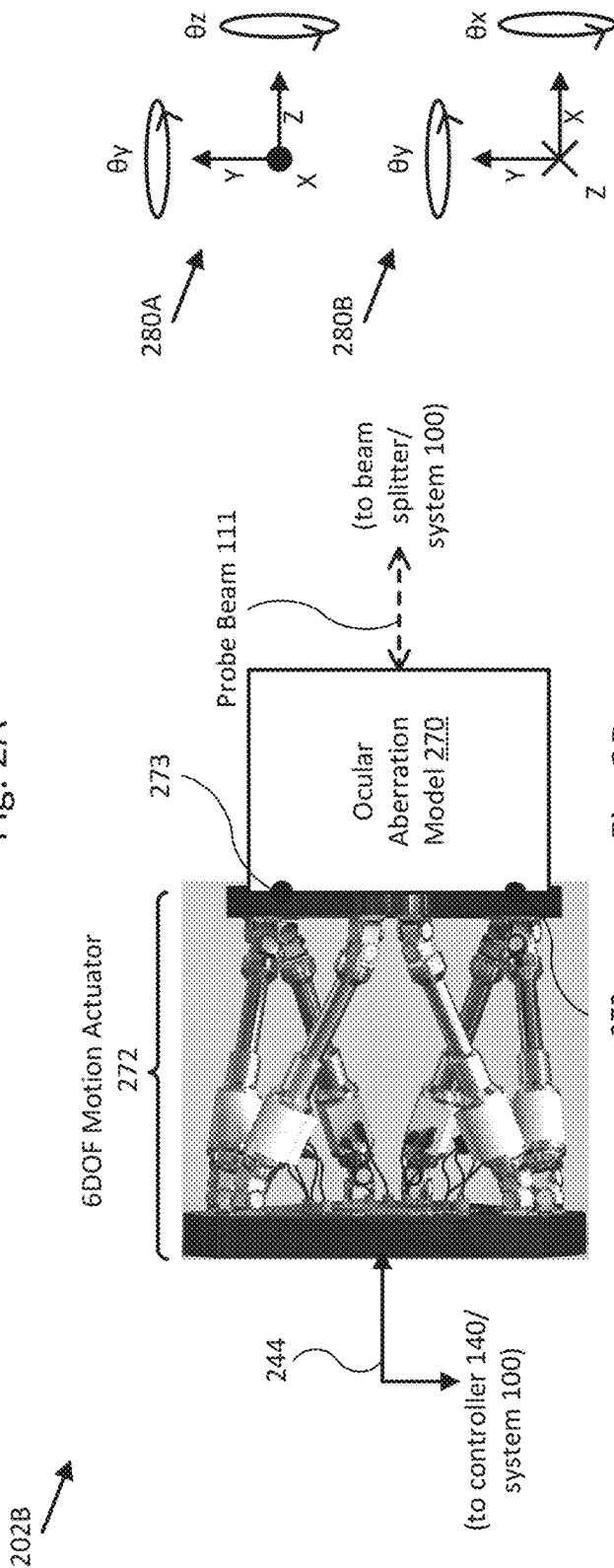
Fig. 2A
Fig. 2B

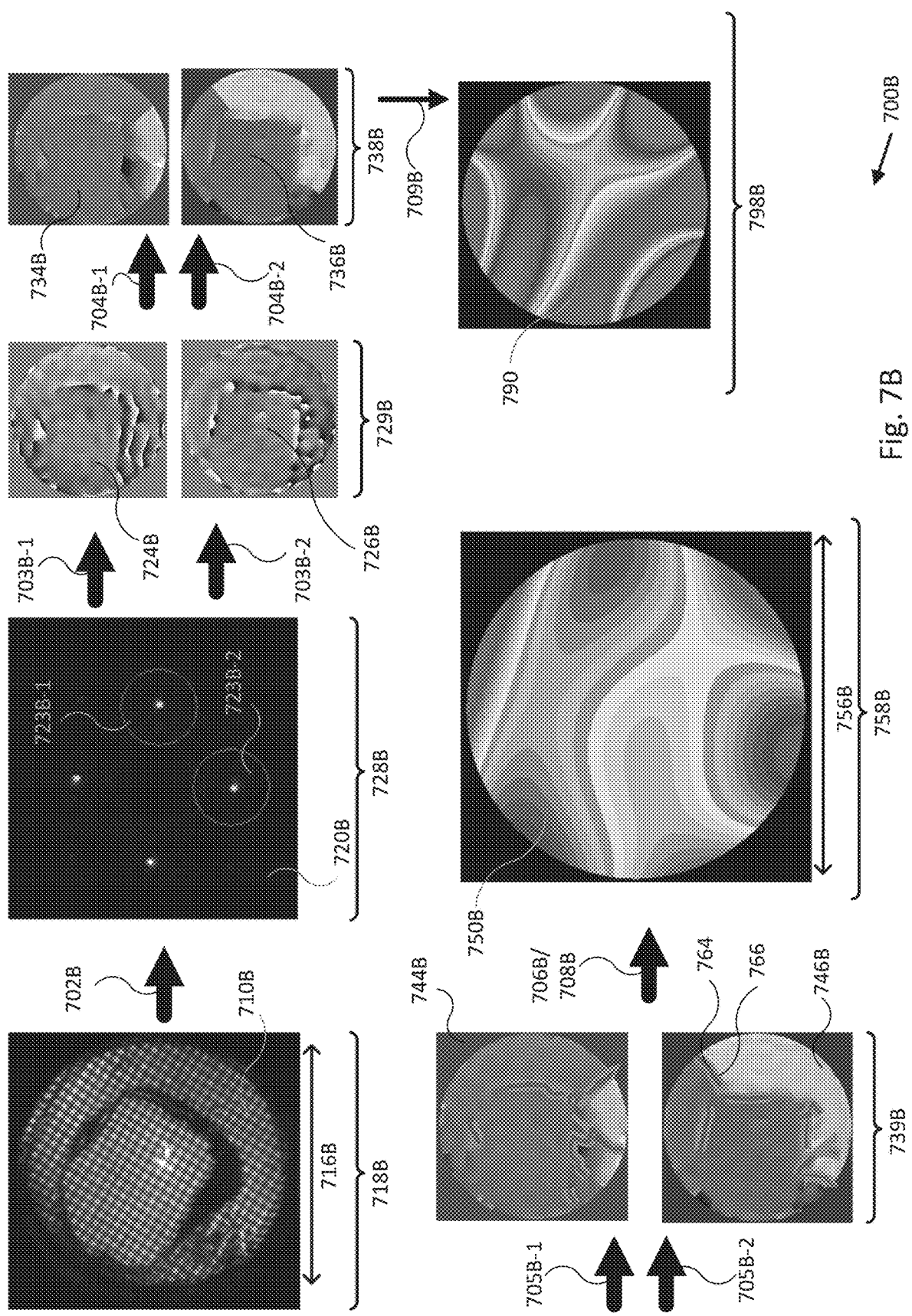

DRY EYE MITIGATION FOR OCULAR ABERROMETRY SYSTEMS AND METHODS

TECHNICAL FIELD

One or more embodiments of the present disclosure relate generally to ocular aberrometry and more particularly, for example, to systems and methods for improving clinical or intraoperative ocular aberrometry.

BACKGROUND

Eye surgery can involve reshaping the cornea and/or surface of the eye, insertion and/or replacement of intraocular devices and/or artificial intraocular lenses (IOLs), and/or other surgical manipulation of the active optical components of the eye. To achieve an optimal post-operative visual outcome, a good pre-operative clinical evaluation and surgical plan, and intraoperative monitoring of the execution of the surgical plan, are crucial.

Ocular aberrometry performed by an ocular aberrometer is typically the general methodology used to characterize an eye prior to surgery, to monitor the progress of the surgery, and to evaluate the success of the surgery. Conventional ocular aberrometers often suffer from a variety of measurement errors associated with eye movement and/or misalignment and optical aberrations of the aberrometer itself, which can lead to an inaccurate surgical plan and suboptimal surgical or vision outcome for a patient. Furthermore, conventional ocular aberrometers often incorporate measurement and characterization techniques that can introduce inaccuracies into the resulting aberration characterization of an eye, thereby complicating recovery of accurate aberrometry of the eye.

Therefore, there is a need in the art for systems and methods to improve clinical and/or intraoperative ocular aberrometry that leads to optimized surgical or vision outcomes for patients.

SUMMARY

Techniques are disclosed for systems and methods to provide improved ocular aberrometry. In accordance with one or more embodiments, an ocular aberrometry system may include a wavefront sensor configured to provide wavefront sensor data associated with an optical target monitored by the ocular aberrometry system and a logic device configured to communicate with the wavefront sensor. The logic device may be configured to determine a complex analysis engine for the ocular aberrometry system based, at least in part, on an aberrometer model and/or an eye model associated with the ocular aberrometry system, wherein the aberrometer model and the eye model are based, at least in part, on wavefront sensor data provided by the wavefront sensor. The logic device may also be configured to generate a compact analysis engine for the ocular aberrometry system based, at least in part, on the determined complex analysis engine In other embodiments, a method may include determining a complex analysis engine for an ocular aberrometry system based, at least in part, on an aberrometer model and/or an eye model associated with the ocular aberrometry system, wherein the aberrometer model and the eye model are based, at least in part, on wavefront sensor data provided by a wavefront sensor of the ocular aberrometry system; and generating a compact analysis engine for the ocular aberrometry system based, at least in part, on the determined complex analysis engine.

According to some embodiments, a non-transitory machine-readable medium may include a plurality of machine-readable instructions which when executed by one or more processors are adapted to cause the one or more processors to perform a method. The method may include determining a complex analysis engine for an ocular aberrometry system based, at least in part, on an aberrometer model and/or an eye model associated with the ocular aberrometry system, wherein the aberrometer model and the eye model are based, at least in part, on wavefront sensor data provided by a wavefront sensor of the ocular aberrometry system; and generating a compact analysis engine for the ocular aberrometry system based, at least in part, on the determined complex analysis engine.

In a further embodiment, an ocular aberrometry system may include a wavefront sensor configured to provide wavefront sensor data associated with an optical target monitored by the ocular aberrometry system and a logic device configured to communicate with the wavefront sensor. The logic device may be configured to receive ocular aberrometry output data including at least the wavefront sensor data provided by the wavefront sensor, determine estimated ocular alignment deviations corresponding to a relative position and/or orientation of the optical target monitored by the ocular aberrometry system based, at least in part, on the received ocular aberrometry output data, and generate user feedback corresponding to the received ocular aberrometry output data based, at least in part, on the estimated ocular alignment deviations.

In other embodiments, a method may include receiving ocular aberrometry output data from an ocular aberrometry system comprising a wavefront sensor, wherein the ocular aberrometry output data includes at least wavefront sensor data associated with an optical target monitored by the ocular aberrometry system, determining estimated ocular alignment deviations corresponding to a relative position and/or orientation of the optical target monitored by the ocular aberrometry system based, at least in part, on the received ocular aberrometry output data, and generating user feedback corresponding to the received ocular aberrometry output data based, at least in part, on the estimated ocular alignment deviations.

According to some embodiments, a non-transitory machine-readable medium may include a plurality of machine-readable instructions which when executed by one or more processors are adapted to cause the one or more processors to perform a method. The method may include receiving ocular aberrometry output data from an ocular aberrometry system comprising a wavefront sensor, wherein the ocular aberrometry output data includes at least wavefront sensor data associated with an optical target monitored by the ocular aberrometry system, determining estimated ocular alignment deviations corresponding to a relative position and/or orientation of the optical target monitored by the ocular aberrometry system based, at least in part, on the received ocular aberrometry output data, and generating user feedback corresponding to the received ocular aberrometry output data based, at least in part, on the estimated ocular alignment deviations.

In a further embodiment, an ocular aberrometry system may include a wavefront sensor configured to provide wavefront sensor data associated with an optical target monitored by the ocular aberrometry system and a logic device configured to communicate with the wavefront sensor. The logic device may be configured to receive ocular aberrometry output data including at least the wavefront sensor data provided by the wavefront sensor, to identify imaging artifact induced singularities in the received ocular aberrometry output data, to determine corrected aberrometry output data based, at least in part, on the identified singularities and the received ocular aberrometry output data, and to generate user feedback corresponding to the received ocular aberrometry output data based, at least in part, on the corrected aberrometry output data.

In other embodiments, a method may include receiving ocular aberrometry output data from an ocular aberrometry system including a wavefront sensor, wherein the ocular aberrometry output data includes at least wavefront sensor data associated with an optical target monitored by the ocular aberrometry system, identifying imaging artifact induced singularities in the received ocular aberrometry output data, determining corrected aberrometry output data based, at least in part, on the identified singularities and the received ocular aberrometry output data, and generating user feedback corresponding to the received ocular aberrometry output data based, at least in part, on the corrected aberrometry output data.

According to some embodiments, a non-transitory machine-readable medium may include a plurality of machine-readable instructions which when executed by one or more processors are adapted to cause the one or more processors to perform a method. The method may include receiving ocular aberrometry output data from an ocular aberrometry system including a wavefront sensor, wherein the ocular aberrometry output data includes at least wavefront sensor data associated with an optical target monitored by the ocular aberrometry system, identifying imaging artifact induced singularities in the received ocular aberrometry output data, determining corrected aberrometry output data based, at least in part, on the identified singularities and the received ocular aberrometry output data, and generating user feedback corresponding to the received ocular aberrometry output data based, at least in part, on the corrected aberrometry output data.

In a further embodiment, an ocular aberrometry system may include a wavefront sensor configured to provide wavefront sensor data associated with an optical target monitored by the ocular aberrometry system and a logic device configured to communicate with the wavefront sensor. The logic device may be configured to receive ocular aberrometry output data including at least the wavefront sensor data provided by the wavefront sensor, to determine a tear film hydration state associated with the optical target based, at least in part, on the received ocular aberrometry output data, and to generate user feedback corresponding to the determined tear film hydration state based, at least in part, on the received aberrometry output data and/or the determined tear film hydration state.

In other embodiments, a method may include receiving ocular aberrometry output data from an ocular aberrometry system including a wavefront sensor, wherein the ocular aberrometry output data includes at least wavefront sensor data associated with an optical target monitored by the ocular aberrometry system, determining a tear film hydration state associated with the optical target based, at least in part, on the received ocular aberrometry output data, and generating user feedback corresponding to the determined tear film hydration state based, at least in part, on the received aberrometry output data and/or the determined tear film hydration state.

According to some embodiments, a non-transitory machine-readable medium may include a plurality of machine-readable instructions which when executed by one or more processors are adapted to cause the one or more processors to perform a method. The method may include receiving ocular aberrometry output data from an ocular aberrometry system including a wavefront sensor, wherein the ocular aberrometry output data includes at least wavefront sensor data associated with an optical target monitored by the ocular aberrometry system, determining a tear film hydration state associated with the optical target based, at least in part, on the received ocular aberrometry output data, and generating user feedback corresponding to the determined tear film hydration state based, at least in part, on the received aberrometry output data and/or the determined tear film hydration state.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 2A-B illustrate block diagrams of aberrometry characterization targets for an ocular aberrometry system in accordance with an embodiment of the disclosure.

FIGS. 7A-C illustrate procedural diagrams of processes to reduce imaging artifact induced error in an ocular aberrometry system in accordance with an embodiment of the disclosure.

Embodiments of the invention and their advantages are best understood by referring to the detailed description that follows. It should be appreciated that like reference numerals are used to identify like elements illustrated in one or more of the figures.

DETAILED DESCRIPTION

Figure 1:
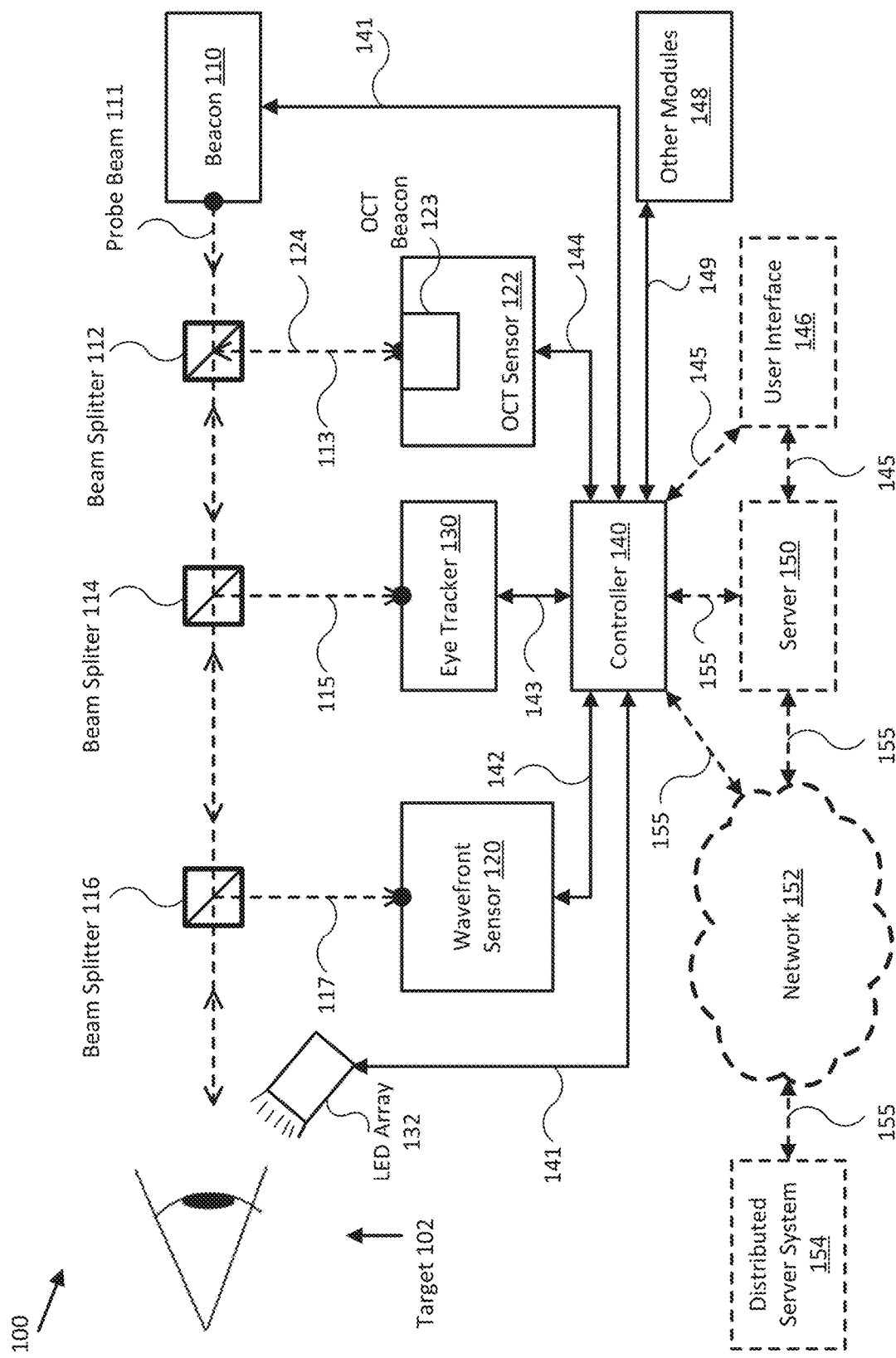
FIG. 1 illustrates a block diagram of an ocular aberrometry system in accordance with an embodiment of the disclosure.

In accordance with various embodiments of the present disclosure, ocular aberrometry systems and methods provide substantially real time measurement and monitoring of aberrations of a patient's eye with reduced system and measurement errors typical of conventional systems. For example, when a patient's eye fixates during an ocular aberration measurement or exam, it will naturally drift. This fixation drift includes tip, tilt, twist rotations of the eye, as well as changes in x, y, and z positions. These alignment deviations cause errors in the calculation of an eye's wavefront-characterized aberrations. If the average of these alignment deviations is close to zero, then averaging wavefront aberration measurements from individual frames of an exam image stream can be sufficient to remove most of the errors caused by misalignment. When the average of the alignment deviations for an exam sequence is known not to be near zero, or it cannot be confirmed that the alignment deviations have a near-zero mean, the measurement error or noise may be reduced using various strategies described herein, including one or a combination of averaging wavefront sensor data (e.g., represented by Zernike polynomial expansions) where the alignment deviation does not exceed a preset threshold, correcting misalignment-based error in the wavefront sensor data using a complex analysis method (described herein), determining a fixation status of the eye (e.g., for each wavefront measurement) based on cluster analysis applied to a series of wavefront measurements and/or based on eye tracker data. Estimated alignment deviations and/or their effects on wavefront measurements may be reduced to an ocular alignment deviation metric and provided to a user of the ocular aberrometry system as a display view with corresponding graphics or used to cause the ocular aberrometry system to ignore an image from an exam image sequence or abort and/or restart an exam. As such, embodiments provide substantially real time monitoring feedback while providing more reliable and accurate aberrometry measurements than conventional systems, such as by decreasing the variability in clinical and intraoperative ocular aberrometry exams due to eye movement during an exam image sequence.

In additional embodiments of the present disclosure, ocular aberrometry systems and methods provide a platform and techniques to accurately characterize system aberrations and correct wavefront sensor data that would otherwise be degraded by alignment deviations associated with the patient's eye. For example, to account for the possible error caused by system aberrations or created during eye motion, ocular aberrometry systems described herein may employ one or more of two unique forms of calibration for accurate high order aberration (HOA) analysis: a system characterization process, and a complex analysis training process.

For the system characterization process, the ocular aberrometry system may be used to measure a series of reference interferograms (e.g., a form of wavefront sensor data) generated by a model target configured to present substantially a single type of variable aberration (e.g., a defocus aberration) to the ocular aberrometry system with substantially zero alignment deviation. The reference interferograms may be used to characterize and/or quantify any system aberrations of the particular ocular aberrometry system, which can be used to correct wavefront sensor data provided by a wavefront sensor of that particular ocular aberrometry system, such as by removing it prior to subsequent analysis.

For the complex analysis training process, the ocular aberrometry system may be used to capture sets of wavefront measurements generated with a model target configured to present a selection of different types and varying strengths of aberrations (e.g., for Zernike expansion coefficients up through $6^{th}$ order) to the ocular aberrometry system with a variable alignment deviation in tip, tilt, twist rotations and x, y, and z positions of the aberration element of the model target. The sets of wavefront measurements may be used to train and/or refine a complex analysis engine executed by the ocular aberrometry system and configured to generate substantially accurate estimated alignment deviations and/or corrected wavefront sensor data based on uncorrected wavefront sensor data, for example, or a combination of uncorrected wavefront sensor data and eye tracker data, as described herein. As such, embodiments provide more reliable and accurate aberrometry measurements than conventional systems, such as by increasing the precision and accuracy of aberrometry measurements due to reduction in errors resulting from system aberrations and off-axis or skewed eye aberrometry measurements. Moreover, embodiments provide a more robust (e.g., reliable and quick) aberrometry system by increasing the range of alignment deviations (e.g., present and/or detected in a given image of an exam image sequence) that may be accurately compensated for or corrected and thus included in a particular exam.

In further embodiments of the present disclosure, ocular aberrometry systems and methods provide techniques to correct wavefront sensor data that would otherwise be degraded by imaging artifacts associated with the patient's eye. For example, to account for the possible error caused by imaging of vitreous bubbles and/or other image artifacts during an eye characterization process, ocular aberrometry systems described herein may decompose wavefront sensor data (e.g., a representation of an interferogram of the eye) into a form including a phase component (e.g., a spatial phase component) that can be weighted to reduce or eliminate the portion of the wavefront sensor data contributing to the error.

In further embodiments of the present disclosure, ocular aberrometry systems and methods provide techniques to monitor tear film hydration (e.g., dry eye) during an aberrometry exam to help mitigate the detrimental effects of dehydration (e.g., relatively low tear film hydration) on corresponding wavefront sensor data. For example, ocular aberrometry systems described herein may provide substantially real-time feedback to a clinician or surgeon so as to, for example, omit wavefront sensor data degraded by relatively poor tear film hydration, prompt for a patient to blink, prompt an operator or surgeon to supply saline, and/or provide other dry eye mitigation techniques, as described herein.

FIG. 1 illustrates a block diagram of an ocular aberrometry system 100 in accordance with an embodiment of the disclosure. In the embodiment shown in FIG. 1, ocular aberrometry system 100 may be implemented to provide substantially real time (e.g., 30 Hz updates) monitoring of an optical target 102 (e.g., a patient's eye) while continuously compensating for common characterization errors, such as patient movement, system optical aberrations, thermal variations, vibrations, and/or other characterization errors that would otherwise degrade the ocular aberrometry provided by ocular aberrometry system 100.

As shown in FIG. 1, ocular aberrometry system 100 includes a beacon 110 generating probe beam 111 that is used to illuminate optical target 102 for wavefront sensor 120 and/or other elements of ocular aberrometry system 100. Ocular aberrometry system 100 may also include various other sensor specific beacons and/or light sources, such as light emitting diode (LED) array 132 used to illuminate optical target 102 for eye tracker 130, and OCT beacon 123 used to generate OCT probe beam 124 to illuminate optical target 102 for OCT sensor 122. Beam splitters 112-116 are used to provide probe beam 111 to optical target 102 and generate associated sensor beams 113, 115, 117 sourced by optical target 102 (e.g., a portion of probe beam 111, probe beam 124, and light generated by LED array 132 reflected by optical target 102). Beacon 110, OCT beacon 123, LED array 132, and each sensor element of ocular aberrometry system 100 may be controlled by controller 140 (e.g., over communication links 141-144), and controller 140 may also serve as an interface between beacon 110, OCT beacon 123, LED array 132, and the sensor elements of ocular aberrometry system 100 and other elements of ocular aberrometry system 100, including user interface 146, server 150, distributed server 154, and other modules 148 (e.g., accessed over optional communication links 145, 149, and 155), as shown.

In typical operation, controller 140 initializes one or more of wavefront sensor 120, optional OCT sensor 122, and optional eye tracker 130, controls beacon 110, OCT beacon 123, and/or LED array 132 to illuminate optical target 102, and receives ocular aberrometry output data (e.g., wavefront sensor data, eye tracker data, OCT sensor data) from the various sensor elements of ocular aberrometry system 100. Controller 140 may process the ocular aberrometry output data itself (e.g., to detect or correct for alignment deviations and/or extract aberrometry parameters from wavefront sensor data) or may provide the ocular aberrometry output data to server 150 and/or distributed server system 154 (e.g., over network 152) for processing, as described herein. Controller 140 and/or server 150 may be configured to receive user input at user interface 146 (e.g., to control operation of ocular aberrometry system 100) and/or to generate user feedback for display to a user via a display of user interface 146, such as display views of the ocular aberrometry output data and/or characteristics of the ocular aberrometry output data, as described herein. Controller 140, server 150, and/or distributed server system 154 may be configured to store, process, and/or otherwise manipulate data associated with operation and/or characterization of ocular aberrometry system 100, for example, including machine learning and/or training of a complex analysis engine (e.g., a neural network based classification and/or regression engine) to characterize system aberrations of ocular aberrometry system 100, detect alignment deviations associated with optical target 102, and/or correct wavefront sensor data and/or associated aberration classification coefficients, as described herein. In various embodiments, ocular aberrometry system 100 may be configured to provide substantially real time monitoring and user feedback (e.g., 30 Hz or higher frequency updates) of the optical aberrometry of optical target 102 while continuously compensating for common characterization errors, as described herein, which makes ocular aberrometry system 100 particularly well suited for clinical and intraoperative examinations.

Beacon 110 may be implemented by a laser source (e.g., producing substantially coherent light) and/or a superluminescent diode (e.g., an "SLD" producing relatively low coherence light) that may be controlled by controller 140 to produce probe beam 111 primarily for use with wavefront sensor 120. OCT beacon 123 may be implemented by a laser source and/or a superluminescent diode (e.g., producing relatively low coherence light, which is particularly suited for OCT sensor 122) that may be controlled by controller 140 to produce OCT probe beam 124 primarily for use with OCT sensor 122. In various embodiments, OCT beacon may be integrated with OCT sensor 122, as shown, may be integrated with beacon 110, for example, and/or may be implemented as its own standalone beacon, similar to beacon 110 (e.g., using an appropriate arrangement of beam splitters). LED array 132 may be implemented by a shaped or patterned array of LEDs that may be controlled by controller 140 to illuminate target 102 primarily for use with eye tracker 130. Beam splitters 112-116 may be implemented by any of a number of optical components (e.g., pellicle beam splitters, mirrored surfaces) configured to aim and/or pass probe beam 111 through to optical target 102 and to divert at least a portion of probe beam 111 and/or a source beam generated by optical target 102 (e.g., a reflected portion of probe beam 111 or 124 and/or the light emitted from LED array 132) towards the various sensor elements of ocular aberrometry system 100 to form sensor beams 113-117 (e.g., sensor beams). Optical target 102 may be a patient eye, for example, or may be implemented by single pass (probe beam 111 is off and optical target 102 generates its own illumination) or double pass (e.g., normal operation with probe beam 111 on) model target, for example, as described herein.

Wavefront sensor 120 may be implemented as any one or combination of devices or device architectures configured to measure the aberrations of an optical wavefront, such as the optical wavefront of sensor beam 117 generated by at least a reflection of probe beam 111 from optical target 102, and wavefront sensor 120 may be configured to provide associated wavefront sensor data. For example, wavefront sensor 120 may be implemented as any one or combination of a Shack-Hartmann wavefront sensor, a phase-shifting Schlieren technique wavefront sensor, a wavefront curvature sensor, a pyramid wavefront sensor, a common-path interferometer, a multilateral shearing interferometer, a Ronchi tester, a shearing interferometer, and/or other wavefront sensor capable of being configured for use in ophthalmology. Wavefront sensor data provided by wavefront sensor 120 may be represented in a variety of formats, including Zernike coefficients, for example, Fourier, Cosine, or Hartley transforms, or Taylor polynomials in cylindrical or cartesian coordinates, or as interferograms.

OCT sensor 122 may be implemented any one or combination of devices or device architectures configured to use relatively low-coherence light and low-coherence interferometry to capture micrometer and/or sub-micrometer resolution two and three dimensional images from within an optical scattering media, such as optical target 102, and be configured to provide associated OCT sensor data. For example, OCT sensor 122 may be implemented as any one or combination of OCT sensor architectures capable of being configured for use in ophthalmology. Eye tracker 130 may be implemented any one or combination of devices or device architectures configured to track the orientation and/or position of optical target 102 and/or a feature of optical target 102 (e.g., a retina, pupil, iris, cornea, lens), including a conventional eye tracker or a fundus camera, and be configured to provide associated eye tracker data. In some embodiments, eye tracker 130 may be configured to capture images of one or more types of Purkinje reflections associated with target 102.

Controller 140 may be implemented as any appropriate logic device (e.g., processing device, microcontroller, processor, application specific integrated circuit (ASIC), field programmable gate array (FPGA), memory storage device, memory reader, or other device or combinations of devices) that may be adapted to execute, store, and/or receive appropriate instructions, such as software instructions implementing a control loop or process for controlling various operations of ocular aberrometry system 100 and/or elements of ocular aberrometry system 100, for example. Such software instructions may also implement methods for processing sensor signals, determining sensor information, providing user feedback (e.g., through user interface 146), querying devices for operational parameters, selecting operational parameters for devices, or performing any of the various operations described herein (e.g., operations performed by logic devices of various devices of ocular aberrometry system 100).

In addition, a machine readable medium may be provided for storing non-transitory instructions for loading into and execution by controller 140. In these and other embodiments, controller 140 may be implemented with other components where appropriate, such as volatile memory, non-volatile memory, one or more interfaces, and/or various analog and/or digital components for interfacing with devices of ocular aberrometry system 100. For example, controller 140 may be adapted to store sensor signals, sensor information, complex analysis parameters, calibration parameters, sets of calibration points, training data, reference data, and/or other operational parameters, over time, for example, and provide such stored data to other elements of ocular aberrometry system 100. In some embodiments, controller 140 may be integrated with user interface 146.

User interface 146 may be implemented as one or more of a display, a touch screen, a keyboard, a mouse, a joystick, a knob, a virtual reality headset, and/or any other device capable of accepting user input and/or providing feedback to a user. In various embodiments, user interface 146 may be adapted to provide user input to other devices of ocular aberrometry system 100, such as controller 140. User interface 146 may also be implemented with one or more logic devices that may be adapted to execute instructions, such as software instructions, implementing any of the various processes and/or methods described herein. For example, user interface 146 may be adapted to form communication links, transmit and/or receive communications (e.g., sensor data, control signals, user input, and/or other information), determine parameters for one or more operations, and/or perform various other processes and/or methods described herein.

In some embodiments, user interface 146 may be adapted to accept user input, for example, to form a communication link (e.g., to server 150 and/or distributed server system 154), to select particular parameters for operation of ocular aberrometry system 100, to select a method of processing sensor data, to adjust a position and/or orientation of an articulated model target, and/or to otherwise facilitate operation of ocular aberrometry system 100 and devices within ocular aberrometry system 100. Once user interface 146 accepts a user input, the user input may be transmitted to other devices of system 100 over one or more communication links. In one embodiment, user interface 146 may be adapted to display a time series of various sensor data and/or other parameters as part of display including a graph or map of such data and/or parameters. In some embodiments, user interface 146 may be adapted to accept user input modifying a control loop or process parameter of controller 140, for example, or a control loop or process parameter of any other element of ocular aberrometry system 100.

Other modules 148 may include any one or combination of sensors and/or devices configured to facilitate operation of ocular aberrometry system 100. For example, other modules 148 may include a temperature sensor configured to measure one or more temperatures associated with operation of one or more elements of ocular aberrometry system 100, a humidity sensor configured to measure ambient humidity about ocular aberrometry system 100, a vibration sensor configured to measure a vibration amplitude and/or presence associated with operation of ocular aberrometry system 100, a patient sensor configured to measure a posture, motion, or other characteristic of a patient supply optical target 102, and/or other sensors capable of providing sensor data helpful to facilitate operation of ocular aberrometry system 100 and/or correct for common system errors typical of operation of ocular aberrometry system 100. In additional embodiments, other modules 148 may include an additional illumination and camera system, similar to the combination of LED array 132 and eye tracker 130, configured to capture images of one or more types of Purkinje reflections associated with target 102.

Server 150 may be implemented similarly to controller 140, for example, and may include various elements of a personal computer or server computer used to store, process, and/or otherwise manipulate relatively large data sets associated with one or multiple patients, for example, including relatively large sets of training data, as described herein, so as to train a neural network or implement other types of machine learning. Distributed server system 154 may be implemented as a distributed combination of multiple embodiments of controller 140 and/or server 150, for example, and may include networking and storage devices and capabilities configured to facilitate storage, processing, and/or other manipulation of relatively large data sets, including relatively large sets of training data, as described herein, so as to train a neural network or implement other types of machine learning in a distributed matter. Network 152 may be implemented as one or more of a wired and/or wireless network, a local area network, a wide area network, the Internet, a cellular network, and/or according to other network protocols and/or topologies.

FIGS. 2A-B illustrate block diagrams of aberrometry characterization targets 202A-B for ocular aberrometry system 100 in accordance with an embodiment of the disclosure. In the embodiment shown in FIG. 2A, aberrometry characterization target 202A may be implemented as a single pass model target configured to characterize optical aberrations associated with ocular aberrometry system 100. As shown in FIG. 2A, aberrometry characterization target/single pass model target 202A includes laser or SLD source 260 generating source beam 211 through lens system 262 and oriented along an optical axis of optical aberration system 100 (e.g., aligned with probe beam 111 exiting beam splitter 116). In various embodiments, source 260 may be configured to generate a diverging spherical wavefront with controllable vergence power, a converging spherical wavefront with controllable vergence power, or a planewave with zero power, for example. Lens system 262 is coupled to linear motion actuator 264 via mount 265, which allows lens system 262 to be moved along its optical axis to vary a defocus aberration of single pass model target 202A to generate a plurality of reference interferograms and corresponding wavefront sensor data (e.g., provided by wavefront sensor 120). Such reference interferograms and/or corresponding wavefront sensor data may be aggregated and stored as aberrometer model 360 of FIG. 3, for example, and be used to correct system aberrations associated with ocular aberrometry system 100, as described herein.

In some embodiments, lens system 262 may be implemented as a National Institute of Standards and Technology (NIST) traceable lens, and linear motion actuator 264 may be implemented as a relatively high precision actuator stage configured to position lens system 262 at a set of positions spaced from source 260 to generate source beam 211 with known and predefined defocus powers (e.g., defocus aberrations), such as −12 to 6 diopters, or 0 to +−5 diopters, in steps of 5.0 D, for example, or higher resolution steps, according to a range of defocus aberrations commonly experienced by patients monitored by ocular aberrometry system 100. A resulting aberrometer model 360 may be used to compensate for a variety of system aberrations, including those attributable to shot noise, thermal variations, and vibrations.

As shown in FIG. 2B, aberrometry characterization target/ double pass model target 202B includes interchangeable ocular aberration model 270 releasably coupled to six degree of freedom (6 DOF) motion actuator 272 via one or more mounts 273, where 6 DOF motion actuator 272 is configured to vary the position and/or orientation of interchangeable ocular aberration model 270 to generate a plurality of selected (e.g., known) alignment deviations (e.g., relative to an optical axis of ocular aberrometry system 100) and a corresponding plurality of sets of wavefront sensor data. Such alignment deviations and corresponding wavefront sensor data may be aggregated and stored as eye model 370 of FIG. 3, for example, and be used to train a complex analysis engine or a compact analysis engine, as described herein, to detect alignment deviations associated with ocular target 102 and correct corresponding wavefront sensor data.

In some embodiments, interchangeable ocular aberration model 270 may form one element of a set of interchangeable ocular aberration models each formed with precise amounts of pre-defined ocular aberrations (e.g., represented by precise and predefined Zernike coefficient amplitudes, such as amplitudes expressed in microns for the Zernike expansion through 6th order). In one embodiment, such interchangeable ocular aberration models may be cut on a contact lens lathe using clear poly (methyl methacrylate) (PMMA). More generally, such interchangeable ocular aberration models may be measured by a $3^{rd}$ party profiler with traceability to NIST for ground truth comparison to measurements performed by ocular aberrometry system 100. In various embodiments, 6 DOF motion actuator 272 may be configured to provide micrometer resolution positioning of interchangeable ocular aberration model 270 along the x, y, and z axes, and microradian orienting of interchangeable ocular aberration model 270 about the θy (tip), θx (tilt), and θz (twist) directions, as shown by representative coordinate frames 280A-B.

In general operation, each interchangeable ocular aberration model 270 in the set (e.g., a set of 10 or more) may be mounted to 6 DOF motion actuator 272 in turn and controller 140 may be configured to control 6 DOF motion actuator 272 to position and/or orient interchangeable ocular aberration model 270 at a set of relative positions and/or orientations (e.g., relative to an optical axis of ocular aberrometry system 100) within a range of alignment deviations commonly experienced by patients monitored by ocular aberrometry system 100. In one embodiment, the set of alignment deviations may include approximately 40,000 different alignment deviations. In various embodiments, the combined set of alignment deviations and corresponding sets of wavefront sensor data (e.g., provided by wavefront sensor 120), may form a supervised data set (e.g., eye model 370), which may be used to determine a complex or compact analysis engine, as described herein. Such analysis engines may be used to compensate for alignment deviations of optical target 102, which may also be measured by eye tracker 130. More generally, the combination of characterizations performed by aberrometry characterization targets 202A-B may be used to compensate for or correct both system aberrations and errors in wavefront sensor data caused by misalignment of optical target 102.

Figure 3:
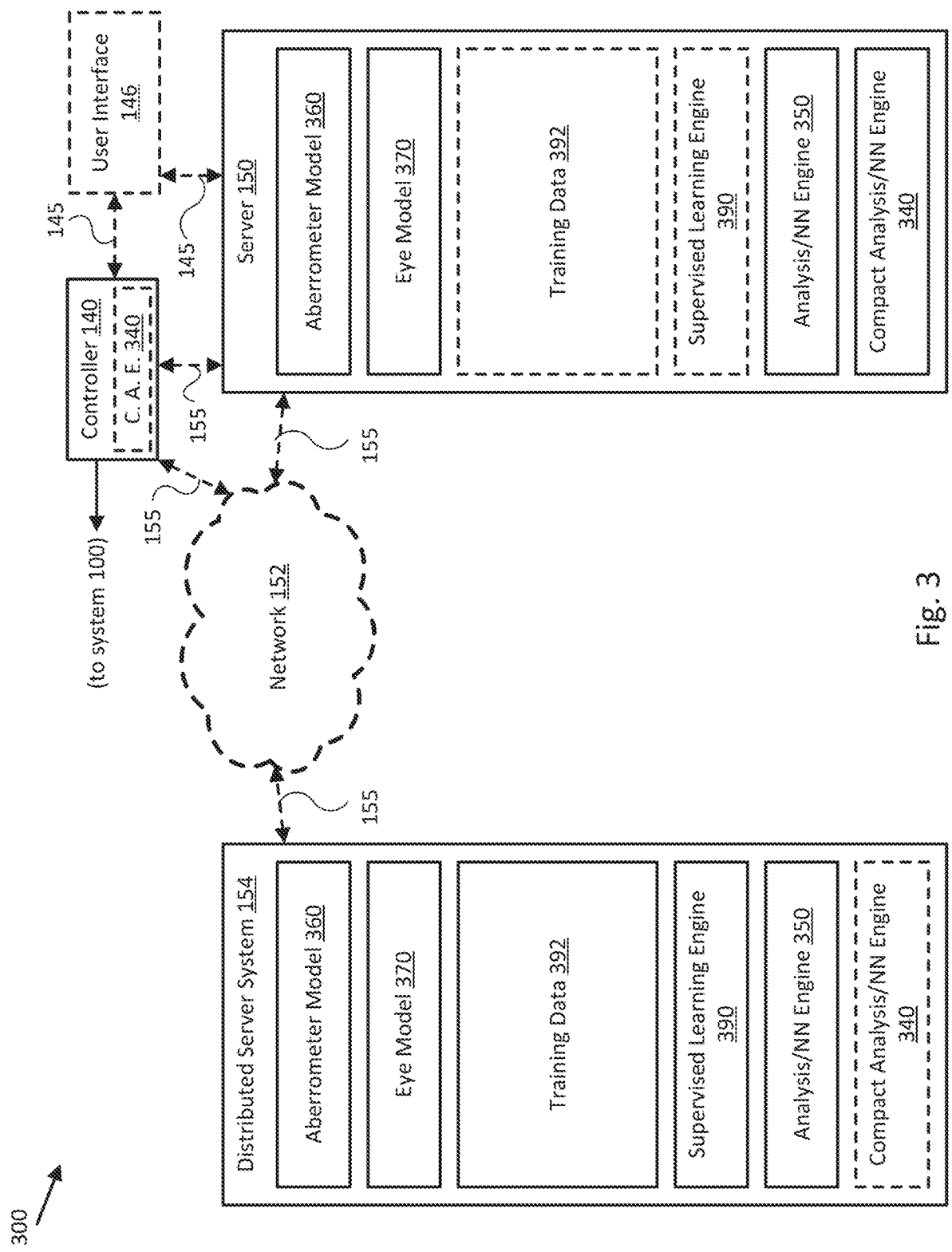
FIG. 3 illustrates a block diagram of an ocular aberrometry system in accordance with an embodiment of the disclosure.

FIG. 3 illustrates a block diagram of an ocular aberrometry system 300 in accordance with an embodiment of the disclosure. In the embodiment shown in FIG. 3, ocular aberrometry system 300 may be configured to use the characterization data generated by ocular aberrometry system 100 via aberrometry characterization targets 202A-B to generate complex analysis engine 350 and/or compact analysis engine 340, which may be used during operation of ocular aberrometry system 100 to provide substantially real time monitoring and user feedback (e.g., 30 Hz or higher frequency updates) of the optical aberrometry of optical target 102 while continuously compensating for common characterization errors, as described herein.

As shown in FIG. 3, ocular aberrometry system 300 is similar to ocular aberrometry system 100 but with additional detail as to various data structures and executable program instructions used in the operation of ocular aberrometry systems 100 or 300. For example, Controller 140 is shown as implemented with compact analysis engine 340, and server 150 and distributed server system 154 are each shown as implemented with or storing one or more of aberrometer model 360, eye model 370, training data 392, supervised learning engine 390, complex analysis/neural network engine 350, and compact analysis engine 340. Dashed lines generally indicate optional storage and/or implementation of a particular element, though in various embodiments, each of controller 140, server 150, and distributed server system 154 may implement or store any of the identified elements and/or additional elements, as described herein.

Figure 6:
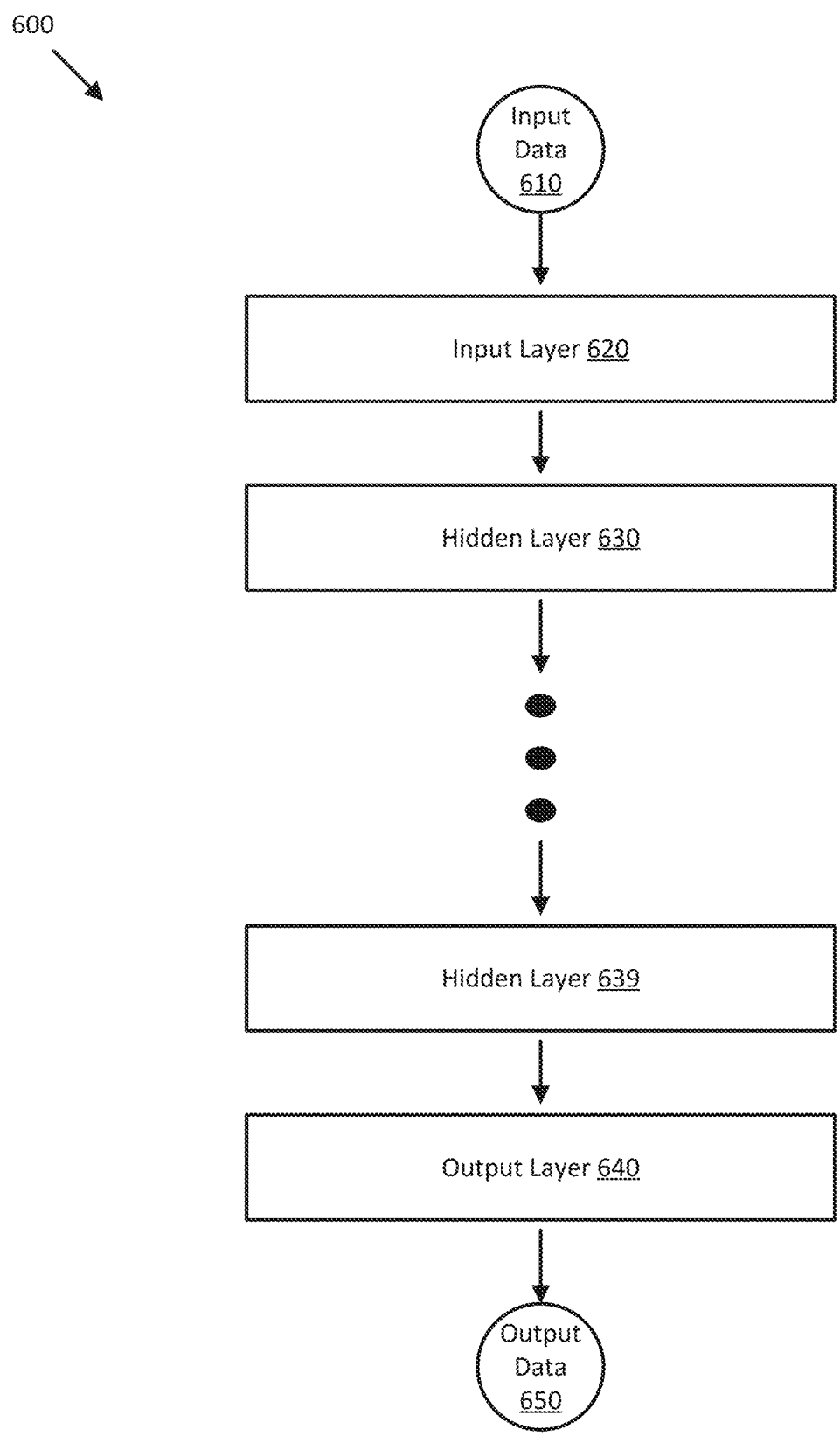
FIG. 6 illustrates a diagram of a multi-layer neural network in accordance with an embodiment of the disclosure.

In general, aberrometer model 360 may be generated by aggregating sensor data associated with use of single pass model target 202A to characterize ocular aberrometry system 100, eye model 370 may be generated by aggregating sensor data associated with use of double pass model target 202B to characterize a parameter space associated with optical target 102, training data 392 may be generated by incorporating aberrometer model 360 and/or eye model 370 and/or by generating and aggregating simulated sets of training data, as described herein with respect to elements of FIG. 6. Supervised learning engine 350 may be implemented as a static learning engine and/or according to a procedurally generated learning engine (e.g., a genetic algorithm updatable learning engine) configured to generate complex analysis engine 350 using training data 392. Complex analysis engine 350 may be implemented as a deep neural network, for example, and/or may be implemented using other complex analysis methodologies, including other various neural network architectures or complex analysis methodologies, including a dense K-nearest neighbor (k-NN) database for classification and/or regression, as described herein. Compact analysis engine 340 may be implemented as a compact form of complex analysis engine 350, such as a form more suited for relatively low resource but high performance execution by controller 140, for example, and as such may be implemented as a deep neural network and/or other complex analysis methodologies. In a particular embodiment, compact analysis engine 340 may be implemented as a neural network with fewer hidden layers and/or neurons/ layer than complex analysis engine 350.

Figure 4:
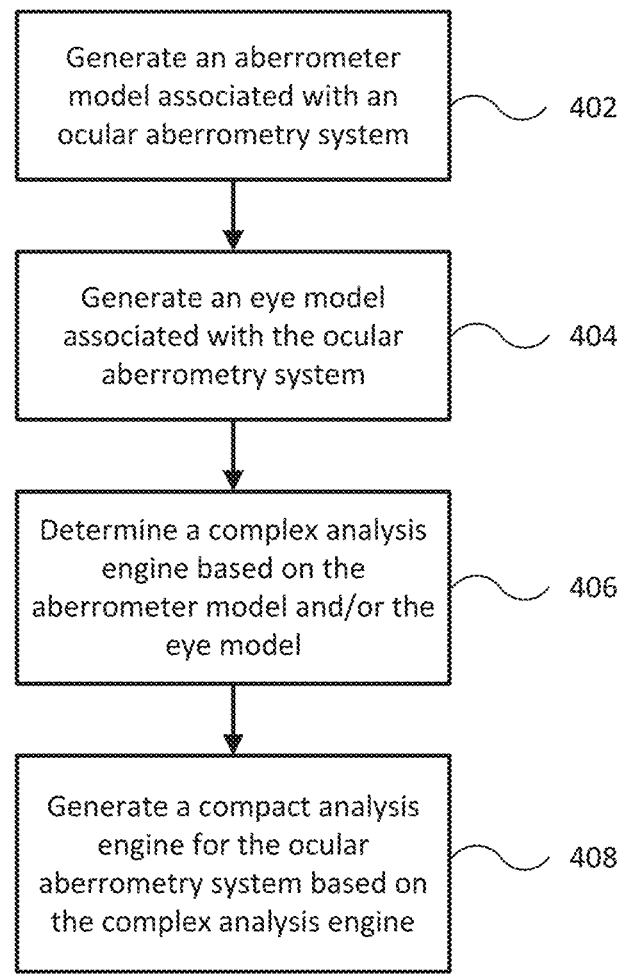
FIG. 4 illustrates a flow diagram of a process to characterize an ocular aberrometry system in accordance with an embodiment of the disclosure.

FIG. 4 illustrates a flow diagram of a process 400 to characterize ocular aberrometry systems 100 and/or 300 in accordance with an embodiment of the disclosure. It should be appreciated that any step, sub-step, sub-process, or block of process 400 may be performed in an order or arrangement different from the embodiments illustrated by FIG. 4. For example, in other embodiments, one or more blocks may be omitted from or added to the process. Furthermore, block inputs, block outputs, various sensor signals, sensor information, calibration parameters, and/or other operational parameters may be stored to one or more memories prior to moving to a following portion of a corresponding process. Although process 400 is described with reference to systems, processes, control loops, and images described in reference to FIGS. 1-3, process 400 may be performed by other systems different from those systems, processes, control loops, and images and including a different selection of electronic devices, sensors, assemblies, mobile structures, and/or mobile structure attributes, for example.

In block 402, an aberrometer model associated with an ocular aberrometry system is generated. For example, controller 140, server 150, and/or distributed server system 154 may be configured to control source 260 of single pass model target 202A, arranged as optical target 102 monitored by ocular aberrometry system 100, to generate source beam 211 through lens system 262 to illuminate wavefront sensor 120 and/or other elements of ocular aberrometry system 100. Controller 140 may be configured to vary a defocus aberration of single pass model target 202A according to a plurality of selected defocus powers, for example, to generate a plurality of sets of wavefront sensor data provided by wavefront sensor 120. Controller 140, server 150, and/or distributed server system 154 may be configured to determine system aberrations associated with ocular aberrometry system 100 based, at least in part, on the plurality of sets of wavefront sensor data provided by wavefront sensor 120. The system aberrations and/or the associated sets of wavefront sensor data may be stored (e.g., on server 150 and/or distributed server system 154) as aberrometer model 360.

In block 404, an eye model associated with an ocular aberrometry system is generated. For example, controller 140, server 150, and/or distributed server system 154 may be configured to control beacon 110 of ocular aberrometry system 100 to generate probe beam 111 to illuminate double pass model target 202B, arranged as optical target 102 monitored by ocular aberrometry system 100, which in turn illuminates (e.g., via reflection of probe beam 111) one or more of wavefront sensor 120, eye tracker 130, OCT sensor 122, and/or other elements of ocular aberrometry system 100. Controller 140 may be configured to vary a position and/or orientation of interchangeable ocular aberration model 270 of double pass model target 202B, relative to optical axis 111 of ocular aberrometry system 100, according to a plurality of selected alignment deviations, for example, to generate a corresponding plurality of sets of wavefront sensor data provided by wavefront sensor 120. The plurality of selected alignment deviations and/or the corresponding plurality of sets of wavefront sensor data may be stored (e.g., on server 150 and/or distributed server system 154) as eye model 370. Similar techniques may be used to incorporate eye tracker data from eye tracker 130 and OCT sensor data from OCT sensor 122 into eye model 370.

In block 406, a complex analysis engine is determined. For example, controller 140, server 150, and/or distributed server system 154 may be configured to determine complex analysis engine 350 based, at least in part, on aberrometer model 360 generated in block 402 and/or eye model 370 generated in block 404. In some embodiments, controller 140, server 150, and/or distributed server system 154 may be configured to form deep neural network 600 including input layer 620, output layer 640, and at least one hidden layer 630-639 coupled between input layer 620 and output layer 640, each comprising a plurality of neurons. Controller 140, server 150, and/or distributed server system 154 may be configured to train, via supervised learning engine 390, at least a trainable weighting matrix W associated with each neuron of the input, output, and hidden layers of neural network 600 using alignment deviations of eye model 370 as ground truth output data and corresponding sets of wavefront sensor data of eye model 370 as training input data, as described herein. The resulting deep neural network may be stored and used as complex analysis engine 350. In other embodiments, controller 140, server 150, and/or distributed server system 154 may be configured to generate a plurality of corrected sets of wavefront sensor data corresponding to the plurality of selected alignment deviations of eye model 370 based, at least in part, on system aberrations associated with the ocular aberrometry system in aberrometer model 360, prior to forming neural network 600 and training one or more complex analysis parameters of neural network 600 using supervised learning engine 390 to determine complex analysis engine 350, as described herein.

In block 408, a compact analysis engine is generated. For example, controller 140, server 150, and/or distributed server system 154 may be configured to form a compact neural network 600 comprising input layer 620, output layer 640, and a single hidden layer 630 coupled between input layer 620 and output layer 640, and to generate a weighting matrix W associated with each neuron of the input, output, and/or hidden layer of compact neural network 600 based, at least in part, on one or more complex analysis parameters associated with a plurality of hidden layers 630-639 of complex analysis engine 350. Upon generation, compact analysis engine 340 may be stored or otherwise integrated with or implemented by controller 140, which can use compact analysis engine 340 to generate substantially real time (e.g., 30 frames/second) user feedback (e.g., display views including various graphics) and reliable and accurate monitoring of ocular alignment deviations, ocular aberrations, and/or other characteristics of optical target 102, as described herein.

Figure 5:
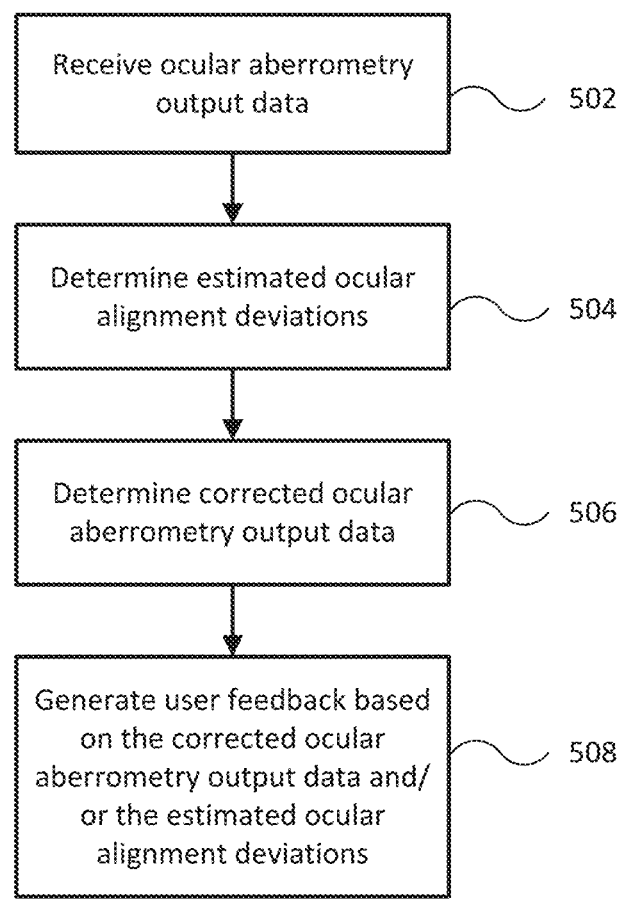
FIG. 5 illustrates a flow diagram of a process to operate an ocular aberrometry system in accordance with an embodiment of the disclosure.

FIG. 5 illustrates a flow diagram of a process 500 to operate ocular aberrometry systems 100 and/or 300 in accordance with an embodiment of the disclosure. It should be appreciated that any step, sub-step, sub-process, or block of process 500 may be performed in an order or arrangement different from the embodiments illustrated by FIG. 5. For example, in other embodiments, one or more blocks may be omitted from or added to the process. Furthermore, block inputs, block outputs, various sensor signals, sensor information, calibration parameters, and/or other operational parameters may be stored to one or more memories prior to moving to a following portion of a corresponding process. Although process 500 is described with reference to systems, processes, control loops, and images described in reference to FIGS. 1-3, process 500 may be performed by other systems different from those systems, processes, control loops, and images and including a different selection of electronic devices, sensors, assemblies, mobile structures, and/or mobile structure attributes, for example.

In block 502, ocular aberrometry output is received. For example, controller 140, server 150, and/or distributed server system 154 may be configured to receive ocular aberrometry output data including at least wavefront sensor data provided by wavefront sensor 120. More generally, the ocular aberrometry output data may include any one or more of wavefront sensor data provided by wavefront sensor 120, OCT sensor data provided by OCT sensor 122, eye tracker data provided by eye tracker 130, and/or other output data provided by ocular aberrometry system 100, as described herein.

In block 504, estimated ocular alignment deviations are determined. For example, controller 140, server 150, and/or distributed server system 154 may be configured to determine estimated ocular alignment deviations corresponding to a relative position and/or orientation of optical target 102 (e.g., a patient's eye) monitored by ocular aberrometry system 100 based, at least in part, on the ocular aberrometry output data received in block 502. In some embodiments, controller 140, server 150, and/or distributed server system 154 may be configured to determine the estimated ocular alignment deviations based, at least in part, on eye tracker sensor data received in block 502. In other embodiments, wavefront sensor data received in block 502 includes a time series of wavefront sensor measurements, and controller 140, server 150, and/or distributed server system 154 may be configured to determine the estimated ocular alignment deviations by determining, for each wavefront sensor measurement, a wavefront-estimated ocular alignment deviation corresponding to the wavefront sensor measurement.

For example, in one embodiment, controller 140, server 150, and/or distributed server system 154 may be configured to determine the estimated ocular alignment deviations by determining, for each wavefront sensor measurement, a corresponding estimated relative position and/or orientation of optical target 102 (e.g., an estimated ocular alignment of optical target 102), identifying one or more clusters of estimated relative positions and/or orientations of the optical target based, at least in part, on one or more preset or adaptive cluster thresholds, determining a fixation alignment based, at least in part, on a centroid of a largest one of the one or more identified clusters, and determining, for each wavefront sensor measurement, an estimated ocular alignment deviation based, at least in part, on a difference between the fixation alignment and the estimated relative position and/or orientation of the optical target corresponding to the wavefront sensor measurement (e.g., a difference between the fixation alignment and the estimated ocular alignments of optical target 102 corresponding to the time series of wavefront sensor measurements). In related embodiments, where ocular aberrometry system 100 includes eye tracker 130, controller 140, server 150, and/or distributed server system 154 may be configured to determine the estimated ocular alignment deviations by determining, for each wavefront sensor measurement, a corresponding fixation status of the optical target based, at least in part, on a fixation threshold parameter and eye tracker sensor data corresponding to the wavefront sensor measurement, and omitting a subset of the wavefront sensor measurements, prior to determining the corresponding estimated relative positions and/or orientations of optical target 102, based, at least in part, on the determined corresponding fixation statuses. For example, such technique may eliminate wavefront sensor measurements acquired while optical target 102 is detected as not fixated, as detected by eye tracker 130.

In block 506, corrected ocular aberrometry output data is determined. For example, controller 140, server 150, and/or distributed server system 154 may be configured to determine corrected ocular aberrometry output data based, at least in part, on the estimated ocular alignment deviations determined in block 504 and/or the wavefront sensor data received in block 502. In some embodiments, where the wavefront sensor data includes a time series of wavefront sensor measurements, controller 140, server 150, and/or distributed server system 154 may be configured to determine the corrected ocular aberrometry output data by determining, for each wavefront sensor measurement, an estimated ocular alignment deviation associated with the wavefront sensor measurement, and generating an average wavefront sensor measurement, as the corrected wavefront sensor measurement, based, at least in part, on each wavefront sensor measurement with an associated estimated ocular alignment deviation that is equal to or less than a preset maximum allowable deviation. Such preset maximum allowable deviation may be selected or set by a manufacturer and/or user of ocular aberrometry system 100.

In other embodiments, controller 140, server 150, and/or distributed server system 154 may be configured to determine the corrected ocular aberrometry output data by determining, for each wavefront sensor measurement, an estimated ocular alignment deviation associated with the wavefront sensor measurement, determining, for each wavefront sensor measurement with an associated estimated ocular alignment deviation that is equal to or less than a preset maximum allowable deviation, a corrected wavefront sensor measurement based, at least in part, on the wavefront sensor measurement and/or the associated estimated ocular alignment deviation, and generating an average wavefront sensor measurement based, at least in part, on the corrected wavefront sensor measurements. For example, controller 140, server 150, and/or distributed server system 154 may be configured to determine the corrected wavefront sensor measurement by applying complex analysis engine 350 or compact analysis engine 340 of ocular aberrometry system 100 to each wavefront sensor measurement to generate corresponding wavefront-estimated ocular alignment deviations and/or corrected wavefront sensor measurements, as described herein.

In block 508, user feedback is generated. For example, controller 140, server 150, and/or distributed server system 154 may be configured to generate user feedback corresponding to the ocular aberrometry output data, received in block 502, based, at least in part, on the estimated ocular alignment deviations determined in block 504. In some embodiments, controller 140, server 150, and/or distributed server system 154 may be configured to generate the user feedback by determining an ocular alignment deviation metric based, at least in part, on the estimated ocular alignment deviations, and reporting the ocular alignment deviation metric via user interface 146 of ocular aberrometry system 100. In other embodiments, controller 140, server 150, and/or distributed server system 154 may be configured to generate the user feedback based, at least in part, on the estimated ocular alignment deviations determined in block 504 and/or the corrected ocular aberrometry output data determined in block 506. In various embodiments, such user feedback may include a substantially real time display view of an ocular alignment deviation metric based, at least in part, on the estimated ocular alignment deviations determined in block 504, a substantially real time display view of an ocular aberration map based, at least in part, on the corrected ocular aberrometry output data determined in block 504, and/or an audible and/or visual alarm indicating at least one of the estimated ocular alignment deviations are larger than a preset maximum allowable deviation, as described herein.

Embodiments of the present disclosure can thus provide substantially real time (e.g., 30 frames/second) user feedback (e.g., display views including various graphics) and reliable and accurate monitoring of ocular alignment deviations, ocular aberrations, and/or other characteristics of optical target 102, as described herein. Such embodiments may be used to assist in a variety of types of clinical and intraoperative eye exams and help provide improved surgical results.

FIG. 6 illustrates a diagram of a multi-layer or "deep" neural network (DNN) 600 in accordance with an embodiment of the disclosure. In some embodiments, neural network 600 may be representative of a neural network used to implement each of the one or more models and/or analysis engines described with respect to systems 100 and/or 300. Neural network 600 processes input data 610 using an input layer 620. In various embodiments, input data 610 may correspond to the aberrometry output data and/or the training data provided to the one or more models and/or analysis engines to generate and/or train the one or more models and/or analysis models, as described herein. In some embodiments, input layer 620 may include a plurality of neurons or nodes that are used to condition input data 610 by scaling, biasing, filtering, range limiting, and/or otherwise conditioning input data 610 for processing by the remaining portions of neural network 600. In other embodiments, input layer 620 may be configured to echo input data 610 (e.g., where input data 610 is already appropriately scaled, biased, filtered, range limited, and/or otherwise conditioned). Each of the neurons in input layer 620 generates outputs that are provided to neurons/nodes in hidden layer 630. Hidden layer 630 includes a plurality of neurons/nodes that process the outputs from input layer 620. In some embodiments, each of the neurons in hidden layer 630 generates outputs that are then propagated through one or more additional hidden layers that end with hidden layer 639. Hidden layer 639 includes a plurality of neurons/nodes that process the outputs from the previous hidden layer. In the embodiment shown in FIG. 6, the outputs of hidden layer 639 are fed to output layer 640. In various embodiments, output layer 640 includes one or more neurons/nodes that may be used to condition the output from hidden layer 639 by scaling, biasing, filtering, range limiting, and/or otherwise conditioning the output from hidden layer 639 to form output data 650. It alternative embodiments, neural network 600 may be implemented according to different neural network or other processing architectures, including a neural network with only one hidden layer, a neural network with recurrent layers, and/or other various neural network architectures or complex analysis methodologies, including a K-nearest neighbor (k-NN) database for classification and/or regression.

In some embodiments, each of input layer 620, hidden layers 630-639, and/or output layer 640 includes one or more neurons. In one embodiment, each of input layer 620, hidden layers 630-639, and/or output layer 640 may include the same number or a different number of neurons. In a particular embodiment, neural network 600 may include a total of approximately 6 layers with up to 2-4 thousand neurons in each layer. In various embodiments, each of such constituent neurons may be configured to receive a combination (e.g., a weighted sum generated using a trainable weighting matrix/vector W) of its inputs x, to receive an optional trainable bias b, and to apply an activation function f to generate an output a, such as according to the equation $a=f(Wx+b)$. Activation function f may be implemented as a rectified linear unit activation function, for example, or any one or combination of an activation function with upper and/or lower limits, a log-sigmoid function, a hyperbolic tangent function, and/or according to other activation function forms. Each neuron in such network may be configured to operate according to the same or a different activation function and/or different type of activation function, as described herein. In a specific embodiment, corresponding to regression applications, only neurons of output layer 640 may be configured to apply such a linear activation function to generate their respective outputs.

In various embodiments, neural network 600 may be trained using supervised learning (e.g., implemented as supervised learning engine 390), such as by systematically providing selected sets of training data (e.g., training data 392) to neural network 600, where each set of training data includes a set of input training data and a corresponding set of ground truth (e.g., expected) output data (e.g., a combination of aberrometer model 360 and eye model 370), and then determining a difference between and/or otherwise comparing resulting output data 650 (e.g., training output data provided by neural network 600) and the ground truth output data (e.g., the "training error"). In some embodiments, the training error may be fed back into neural network 600 to adjust the various trainable weights, biases, and/or other complex analysis parameters of neural network 600. In some embodiments, such training error may be provided as feedback to neural network 600 using one or a variety of back propagation techniques, including a stochastic gradient descent technique, for example, and/or other back propagation techniques. In one or more embodiments, a relatively large group of selected sets of training data may be presented to neural network 600 multiple times until an overall loss function (e.g., a mean-squared error based on the differences of each set of training data) converges to or below a preset maximum allowable loss threshold.

In additional embodiments, supervised learning engine 390 may be configured to include semi-supervised learning, weakly supervised learning, active learning, structured prediction, and/or other generalized machine learning techniques to help train complex analysis parameters of neural network 600 (e.g., and generate complex analysis engine 350), as described herein. For example, supervised learning engine 390 may be configured to generate simulated sets of training data, each set including a simulated input training data and a corresponding set of simulated ground truth output data, and perform supervised learning based, at least in part, on the simulated sets of training data. Each of the simulated sets of input training data and ground truth data may be generated by modifying the input training data (e.g., to adjust an aberration parameter and/or alignment deviation associated with a simulated double pass model target) and interpolating non-simulated ground truth data to generate corresponding simulated ground truth data. In various embodiments, supervised learning engine 390 may be configured to simulate one or many millions of sets of simulated training data, each deviating at least slightly from the sets of training data corresponding to eye model 370, and train neural network 600 according to the one or many millions of sets of such simulated training data.

In various embodiments, ocular aberrometry systems 100 and/or 300 may be configured as a phase-based ocular aberrometry system. In such embodiments, one of the processing steps of such phase-based ocular aberrometry system produces a wrapped-phase array as part of a representation of the wavefront sensor data provided by wavefront sensor 120. Typically, a wrapped-phase array has real values that are limited to the range of $[-\pi$ to $\pi]$ or $[0$ to $2\pi]$ as a natural consequence of calculating the phase from a complex number, for example, using the arc-tangent function. These wrapped phase values are then "unwrapped" to reveal the true range of phase values, which are generally proportional to the first-order wavefront aberration derivatives and may be used to determine wavefront aberration values for a wavefront aberration characterization.

To generate an accurate final set of wavefront aberration values (e.g., Zernike polynomial coefficients), a resulting unwrapped-phase array should be roughly continuous (e.g., correspond to a continuous function). However, for various reasons, such as image artifacts (in the initial interferogram captured by the wavefront sensor) caused by vitreous bubbles, a typical unwrapped-phase array may include various "singularities" or discontinuities and not be continuous, which can lead to errors in a final calculated aberration fit. In general, such aberration fit is usually to a Zernike polynomial expansion, but other functional aberration characterizations are possible. Because of the way the Zernike polynomial coefficients are fit to the wavefront sensor data in the scaled, unwrapped-phase array, a local singularity error (e.g., points where the unwrapped-phase is not continuous) can cause errors over the entire final aberration characterization result. A repair of some type may be applied in the attempt to recover the true phase, but such repair process is often not satisfactory as the "repaired" data points do not accurately reflect the real wavefront sensor data and can introduce additional error. Rather than attempt this type of repair, embodiments disclosed herein apply a linear system of weighted normal equations to the wavefront sensor data represented by the unwrapped-phase array as the Zernike polynomial coefficients are fit to the data in a least squared error sense. The weights of the individual rows in the liner system of equations are chosen to reduce or eliminate the effect of each singularity.

In one embodiment, the weights may be chosen as follows: let d be the closest distance from a point in the unwrapped-phase array to an identified singularity. The weight for the point is: 0 if the distance d is less than or equal to a threshold D0; 1 if the distance d is greater than or equal to a threshold D1; and $[(d-D0)/(D1-D0)]^p$ if the distance d is between D0 and D1. Put differently, the weight for each point is: zero for elements closer than or equal to threshold distance D0 away from any identified singularity; one for elements greater than or equal to threshold distance D1 away from all identified singularities; and a function of the nearest distance, the thresholds, and a scaling parameter p for all elements between the two threshold distances away from an identified singularity. Formulaically:

$$w_i = \begin{cases} 0 & \text{if } d \leq D0 \\ \left(\dfrac{d-D0}{D1-D0}\right)^p & \text{if } D0 < d < D1 \\ 1 & \text{if } D1 \leq d \end{cases} \quad (1)$$

The hyperparameters D0, D1, and p may be optimized depending upon the application, but preferred values are: D0=P*0.05, D1=P*0.1, and p=2, where the value P is the diameter of the pupil being characterized/reconstructed. In various embodiments, such weighted fit decreases the variability in phase-based ocular aberrometry exams caused by singularities in the wavefront sensor data, without risking introduction of new errors, as described herein, which in turn improves the precision and accuracy of the resulting ocular aberrometry output data (e.g., the characterizations of the aberrations in the eye).

Figure 7A:
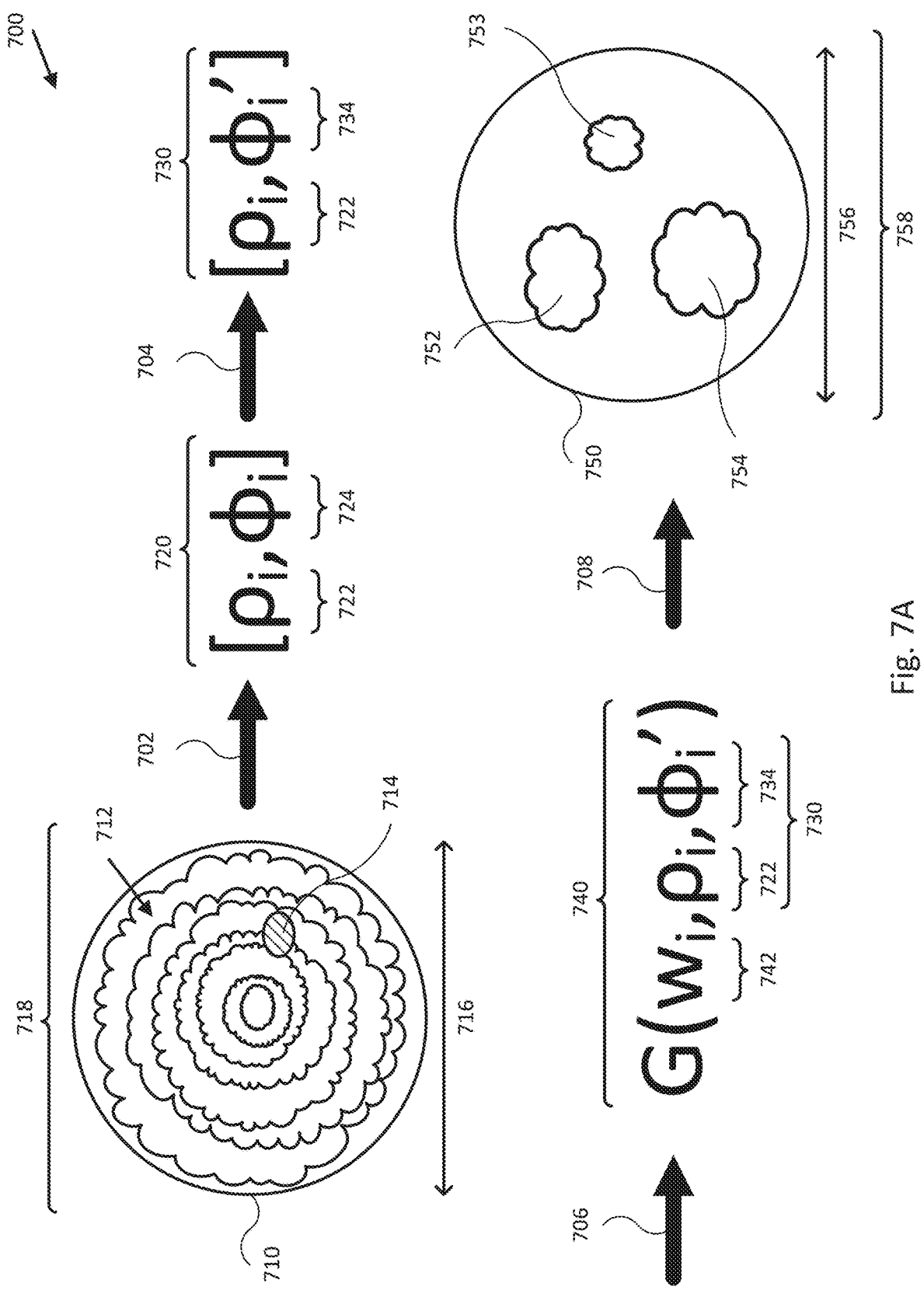

FIG. 7A illustrates a procedural diagram of a process 700 to reduce imaging artifact induced error in an ocular aberrometry system in accordance with an embodiment of the disclosure. In the embodiment shown in FIG. 7A, initial wavefront sensor data in the form of an interferogram 710 of a human eye (e.g., including multiple roughly concentric fringe lines/pattern 712) may be decomposed (e.g., step 702) into a set of wrapped-phase wavefront sensor data 720 including at least wrapped-phase component/array 724 ($\phi_i$). Wrapped-phase wavefront sensor data 720 may include additional components (e.g., amplitude/scaling array 722 ($\rho_i$) such that wrapped-phase wavefront sensor data 720 forms a discrete representation of interferogram 710, which may be analogous to a discrete spatial Fourier transform of interferogram 710. Wrapped-phase wavefront sensor data 720 may be converted (e.g., step 704) into unwrapped-phase wavefront sensor data 730 including at least unwrapped-phase array 734 ($\phi_i'$) by identifying discontinuities (e.g., between adjacent elements) in wrapped-phase array 724 ($\phi_i$) that are approximately $2\pi$ in magnitude (or multiples thereof) and/or that occur near the artificial numerical boundaries of wrapped-phase array 724 ($\phi_i$) (e.g., $+-\pi$ or 0 and $2\pi$) and adding a to or subtracting a from elements of wrapped-phase array 724 ($\phi_i$) to eliminate the discontinuities and form unwrapped-phase array 734 ($\phi_i'$).

Once unwrapped-phase wavefront sensor data 730 is determined, singularities or discontinuities attributed to image artifacts (e.g., related to vitreous bubble 714 imaged as part of interferogram 710) may be identified in the unwrapped-phase wavefront sensor data 730, such as by identifying any remaining discontinuities in unwrapped-phase array 734 (V) with magnitudes greater than a predetermined singularity threshold (e.g., supplied by a user or a manufacturer of ocular aberrometry systems 100 and/or 300). Such predetermined singularity threshold may be selected to account for various types of image noise in interferogram 710 and/or expected slopes between adjacent elements in unwrapped-phase array 734 ($\phi_i'$).

Once such discontinuities are identified (e.g., as elements of unwrapped-phase array 734 ($\phi_i'$), the distance between any element of unwrapped-phase wavefront sensor data 730 and such discontinuities may be determined, and a fitting weight may be determined for each element of unwrapped-phase wavefront sensor data 730, such as by using the linear system of weighted normal equations for $w_i$ (1), as described herein. In some embodiments, such weight may be calculated for the nearest singularity only (e.g., as the value for d), or may be calculated for each detected singularity, and the resulting set of weights combined (e.g., by multiplication) to determine the fitting weight for that element of unwrapped-phase wavefront sensor data 730. An aberration characterization fit 740 (e.g., aberrometry output data) may be determined based on a fitting function (e.g., the selected aberration characterization function, such as a Zernike polynomial expansion of a selected order), the determined weights $w_i$, and unwrapped-phase wavefront sensor data 730 (step 706), and an ocular aberration map 750 may be generated (step 708) to visualize the aberration characterization fit 740 and identify spatial areas 752-754 of an examined eye that deviate from an ideal eye.

In various embodiments, interferogram 710 and/or ocular aberration map 750 may form at least part of a display view (e.g., display views 718 and/or 758) rendered on a display of user interface 146 and displayed to a user as user feedback with regard to the operation of ocular aberrometry systems 100 and/or 300. In general operation, diameter 716 of interferogram 710 and diameter 756 of ocular aberration map 750 may be configured to represent or correspond to roughly the diameter of the pupil of the examined eye.

FIG. 7B illustrates a procedural diagram of a process 700B to reduce imaging artifact induced error in an ocular aberrometry system in accordance with an embodiment of the disclosure, similar to process 700 of FIG. 7A. In the embodiment shown in FIG. 7B, initial wavefront sensor data in the form of an interferogram/fringe pattern 710B may be decomposed (e.g., steps 702B and 703B-1 and 703B-2) into a set of wrapped-phase wavefront sensor data 724B and 726B including at least a wrapped-phase component/array (e.g. similar to wrapped-phase component/array 724 ($\phi_i$) in FIG. 7A). In particular, interferogram 710B may be Fourier transformed (e.g., step 702B) to produce transformed wavefront sensor data 720B, which may include multiple spatial peaks with corresponding spatial structure neighborhoods 723B-1, 723B-2. Spatial structure neighborhoods 723B-1, 723B-2 may in some embodiments be selected to be circular neighborhoods within transformed wavefront sensor data 720B with radiuses selected to include non-overlapping spatial structure relevant to one or more selected aberration characterization function orders (e.g., Zernike polynomial expansion orders), for example, as shown. In some embodiments, each spatial structure neighborhood 723B-1, 723B-2 may be processed separately to determine corresponding sets of wrapped-phase wavefront sensor data 724B and 726B, as shown. In the particular embodiment shown in FIG. 7B, spatial structure neighborhood 723B-1 is processed into a first wrapped-phase dW/dx array and spatial structure neighborhood 723B-1 is processed into a second wrapped-phase dW/dy array.

Wrapped-phase wavefront sensor data 724B and 726B may be converted (e.g., steps 704B-1 and 704B-2) into unwrapped-phase wavefront sensor data 734B, 736B including at least an unwrapped-phase array (e.g. similar to wrapped-phase component/array 734 ($\phi_i'$) in FIG. 7). Once unwrapped-phase wavefront sensor data 734B, 736B is determined, singularities or discontinuities 764 (e.g., attributed to image artifacts of interferogram 710B) may be identified in the unwrapped-phase wavefront sensor data 734B, 736B to generate processed unwrapped-phase wavefront sensor data 744B, 746B. Once such discontinuities 764 are identified (e.g., as elements of the corresponding unwrapped-phase array), the distance between any element of unwrapped-phase wavefront sensor data 734B, 736B and such discontinuities may be determined, and a fitting weight may be determined for each element of unwrapped-phase wavefront sensor data 734B, 736B, such as by equation (1) for $w_i$, as described herein. In particular, processed unwrapped-phase wavefront sensor data 744B, 746B includes darker lines 764 indicating singularities in processed unwrapped-phase wavefront sensor data 744B, 746B and halos 766 about discontinuities 764 indicating localized weights different from 1, for example.

An aberration characterization fit (e.g., aberrometry output data) may be determined based on a fitting function (e.g., the selected aberration characterization function, such as a Zernike polynomial expansion of a selected order or range of orders), the determined weights $w_i$, and processed unwrapped-phase wavefront sensor data 744B, 746B (e.g., a processed form of the first wrapped-phase dW/dx array and the second wrapped-phase dW/dy array), and an ocular aberration map 750B may be generated (step 706B/708B) to visualize the aberration characterization fit and identify various spatial areas (e.g., shown as a color mapped gradient according to a selected palette) of an examined eye that deviate from an ideal eye. Uncorrected ocular aberration map 790B derived directly from unwrapped-phase wavefront sensor data 734B, 736B (step 709B) without weighting according to equation (2) (e.g., showing a significantly different spatial gradient and aberration distribution) is provided in FIG. 7B for comparison.

In various embodiments, interferogram 710B and/or ocular aberration map 750B may form at least part of a display view (e.g., display views 718B and/or 758B) rendered on a display of user interface 146 and displayed to a user as user feedback with regard to the operation of ocular aberrometry systems 100 and/or 300, along with or separate from any one or combination of display views of interstitial steps, such as display views 728B, 729B, 738B, 739B, and/or 798B, as shown. In general operation, diameter 716B of interferogram 710B and diameter 756B of ocular aberration map 750B may be configured to represent or correspond to roughly the diameter of the pupil of the examined eye.

Figure 7C:
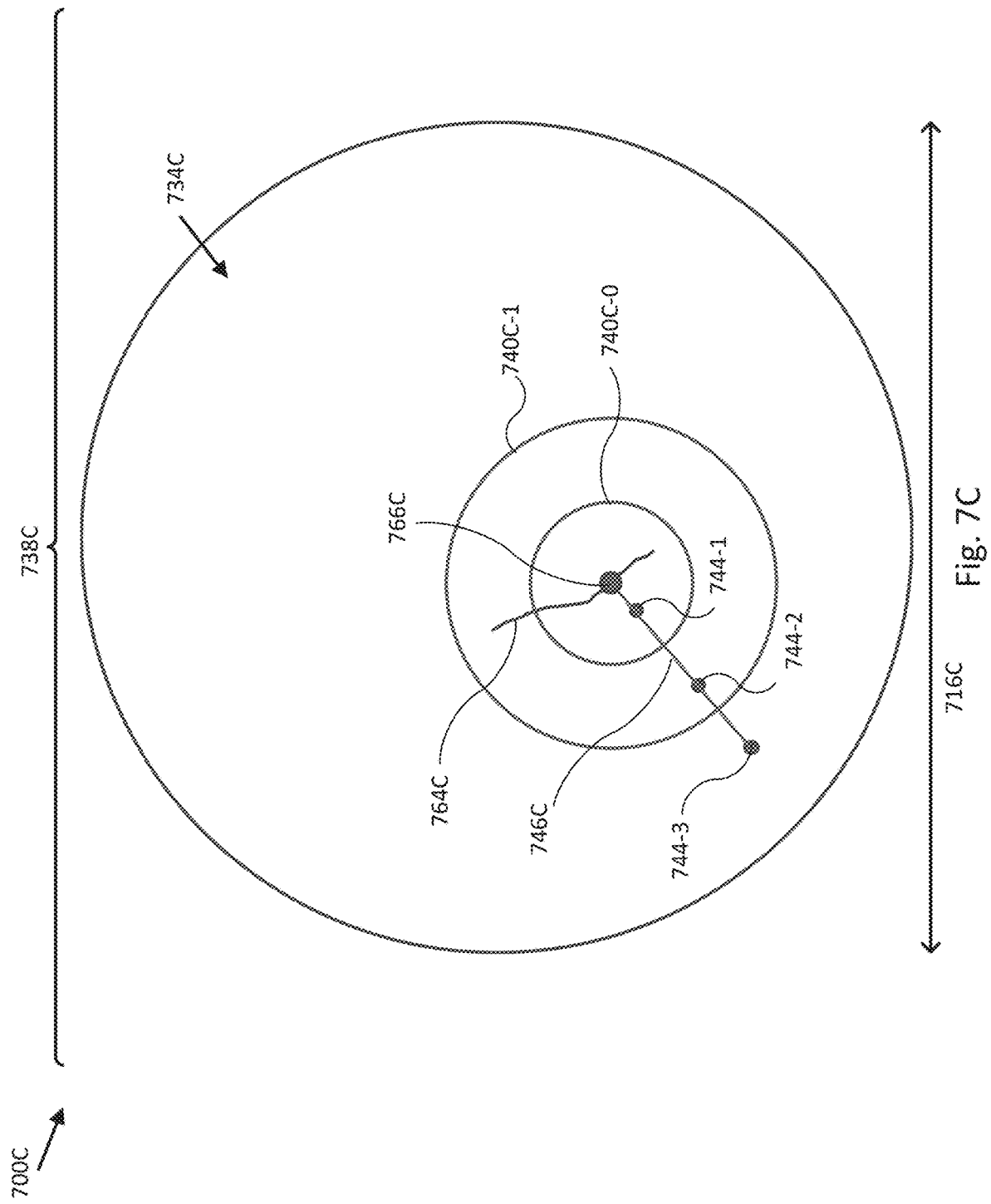

FIG. 7C illustrates a procedural diagram of a process 700C to reduce imaging artifact induced error in an ocular aberrometry system in accordance with an embodiment of the disclosure, including portions of process 700 of FIG. 7A and/or process 700B of FIG. 7B. In particular, process 700C illustrates a spatially exaggerated version of the technique used in steps 705B-1 and 705B-2 to determine and apply weights to unwrapped-phase wavefront sensor data 734B, 736B in light of discontinuities 764. For example, unwrapped-phase wavefront sensor data 734C is shown including discontinuity contour 764C and nearest discontinuity point 766C to elements/points 744-1, 744-2, 744-3 of unwrapped-phase wavefront sensor data 734C (e.g., points used to fit a Zernike polynomial expansion). Also shown in FIG. 7C are circle 740C-0, which encompasses/differentiates all points less than or equal to threshold distance/radius D0 from nearest discontinuity point 766C of discontinuity contour 764C, and circle 740C-1, which excludes/differentiates all points greater than or equal to threshold distance D1 from nearest discontinuity point 766C of discontinuity contour 764C. Line 746C may be perpendicular to discontinuity contour 764C at nearest discontinuity point 766C and passing through elements/points 744-1, 744-2, 744-3 of unwrapped-phase wavefront sensor data 734C. Thus, according to equation (1) herein, the weight of element 744-1 would be zero (e.g., corresponding to discontinuity 764), the weight of element 744-2 would be between zero and one (e.g., corresponding to halo 766), and the weight of element 744-3 would be one (e.g., the remaining portions of unwrapped-phase wavefront sensor data 736B).

In various embodiments, process 700C may form at least part of a display view (e.g., display view 738C) rendered on a display of user interface 146 and displayed to a user as user feedback with regard to the operation of ocular aberrometry systems 100 and/or 300, along with or separate from any one or combination of other display views described herein. In general operation, diameter 716C may be configured to represent or correspond to roughly the diameter of the pupil of the examined eye.

Figure 8:
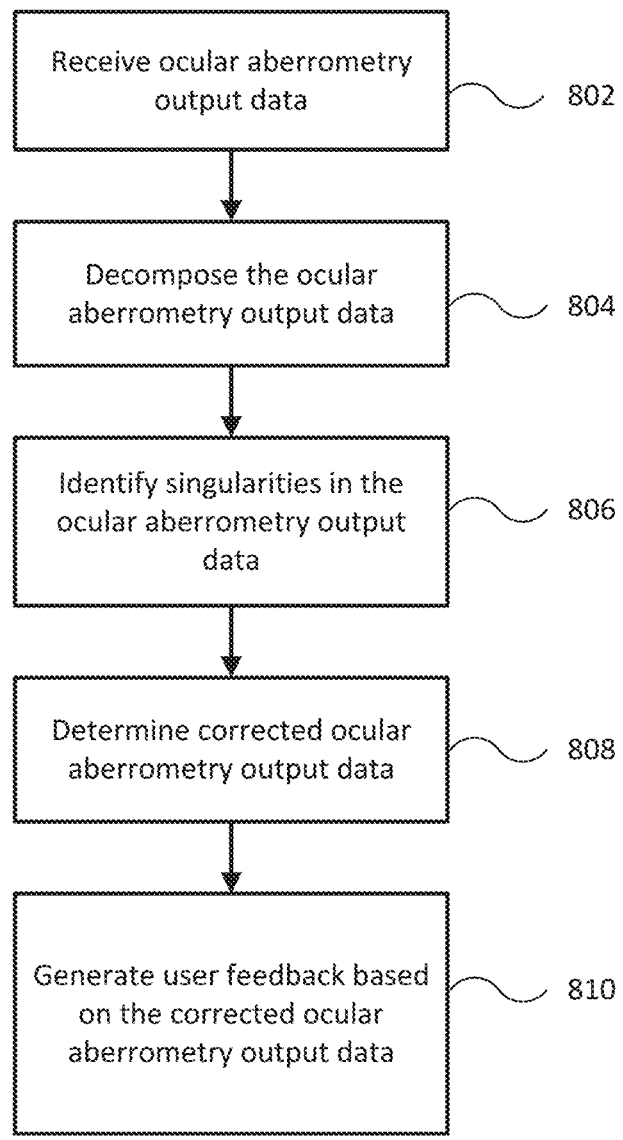
FIG. 8 illustrates a flow diagram of a process to operate an ocular aberrometry system in accordance with an embodiment of the disclosure.

FIG. 8 illustrates a flow diagram of a process 800 to operate ocular aberrometry systems 100 and/or 300 with reduced imaging artifact induced error in accordance with an embodiment of the disclosure. It should be appreciated that any step, sub-step, sub-process, or block of process 800 may be performed in an order or arrangement different from the embodiments illustrated by FIG. 8. For example, in other embodiments, one or more blocks may be omitted from or added to the process. Furthermore, block inputs, block outputs, various sensor signals, sensor information, calibration parameters, and/or other operational parameters may be stored to one or more memories prior to moving to a following portion of a corresponding process. Although process 800 is described with reference to systems, processes, control loops, and images described in reference to FIGS. 1-7, process 800 may be performed by other systems different from those systems, processes, control loops, and images and including a different selection of electronic devices, sensors, assemblies, mobile structures, and/or mobile structure attributes, for example.

In block 802, ocular aberrometry output is received. For example, controller 140, server 150, and/or distributed server system 154 may be configured to receive ocular aberrometry output data including at least wavefront sensor data provided by wavefront sensor 120. More generally, the ocular aberrometry output data may include any one or more of wavefront sensor data provided by wavefront sensor 120, OCT sensor data provided by OCT sensor 122, eye tracker data provided by eye tracker 130, and/or other output data provided by ocular aberrometry system 100, as described herein. Wavefront sensor data provided by wavefront sensor 120 may include interferogram 710 of an examined eye, for example, and/or may include wrapped-phase wavefront sensor data 720 or unwrapped-phase wavefront sensor data 730, for example, depending on the capability and/or configuration of wavefront sensor 120.

In block 804, ocular aberrometry output data is decomposed. For example, controller 140, server 150, and/or distributed server system 154 may be configured to decompose the wavefront sensor data received in block 802 into at least wrapped-phase component/array 724, such as by generating a discrete Fourier transform of interferogram 710, as described herein. In embodiments where wavefront sensor 120 provides wrapped-phase wavefront sensor data 720 directly, block 804 may be omitted or incorporated into block 802, for example.

In block 806, singularities in ocular aberrometry output data are identified. For example, controller 140, server 150, and/or distributed server system 154 may be configured to identify imaging artifact induced singularities in unwrapped-phase wavefront sensor data corresponding to ocular aberrometry output data received in block 802. In some embodiments, controller 140, server 150, and/or distributed server system 154 may be configured to determine unwrapped-phase array 734 and/or unwrapped-phase wavefront sensor data 730 based, at least in part, on wrapped-phase array 724 of wrapped-phase wavefront sensor data 720 and identify imagery artifact induced discontinuities in unwrapped-phase array 734, as described herein. In various embodiments, controller 140, server 150, and/or distributed server system 154 may be configured to identify singularities by identifying discontinuities in unwrapped-phase component 734 of wrapped-phase wavefront sensor data 730 with magnitudes greater than a predetermined singularity threshold, for example, or using other discontinuity detection techniques for discrete data, including spline fitting and element excursion techniques and/or numerical derivative and thresholding techniques, for example.

In block 808, corrected ocular aberrometry output data is determined. For example, controller 140, server 150, and/or distributed server system 154 may be configured to determine corrected ocular aberrometry output data based, at least in part, on wrapped-phase component/array 724 of wrapped-phase wavefront sensor data decomposed in block 804 and/or received in block 802 and/or singularities in the received ocular aberrometry output data identified in block 806. In some embodiments, controller 140, server 150, and/or distributed server system 154 may be configured to determine a fitting weight for each element of unwrapped-phase wavefront sensor data 730 and determine corrected ocular aberrometry output data by determining an aberrometry fit based, at least in part, on the fitting weights and unwrapped-phase wavefront sensor data 730, as described herein.

In some embodiments, controller 140, server 150, and/or distributed server system 154 may be configured to determine the fitting weight for each element of unwrapped-phase wavefront sensor data 730 based on equation (1) for $w_i$, as described herein, where the values of the parameters used in equation (1) are at least partially based on the diameter of the pupil of the eye being examined, such that the fitting weights are themselves based, at least in part, on the pupil diameter. In related embodiments, controller 140, server 150, and/or distributed server system 154 may be configured to determine corrected ocular aberrometry output data additionally employing any of the methods described herein to compensate for system aberrations and/or ocular alignment deviations, as described herein with respect to processes 400 and 500 and FIGS. 4-6.

In block 810, user feedback is generated. For example, controller 140, server 150, and/or distributed server system 154 may be configured to generate user feedback corresponding to the ocular aberrometry output data received in block 802, such as a display view of interferogram 710, and/or to generate user feedback corresponding to the corrected ocular aberrometry output data determined in block 808, such as a display view of ocular aberration map 750. In various embodiments, controller 140, server 150, and/or distributed server system 154 may be configured to generate user feedback using any of the processes described herein with respect to FIGS. 4-6. In various embodiments, such user feedback may include a substantially real time display view of wavefront sensor data received in block 802, decomposed ocular aberrometry output data determined in block 804, singularities identified in block 806, corrected ocular aberrometry output data determined in block 808, and/or a corresponding ocular aberration map 750.

Embodiments of the present disclosure can thus provide substantially real time (e.g., 30 frames/second) user feedback (e.g., display views including various graphics) and reliable and accurate monitoring of ocular aberrations, and/or other characteristics of optical target 102, as described herein. Such embodiments may be used to assist in a variety of types of clinical and intraoperative eye exams and help provide improved surgical results.

Aberrometry measurements can be increasingly negatively impacted in terms of accuracy and repeatability as tear film hydration degrades over the course of an exam/surgery. This can occur due to a lack of basic saline solution applied by a surgeon during an intraoperative measurement or lack of a regular blink by the patient during a clinical exam. In various embodiments, ocular aberrometry systems 100 and/or 300 may be configured to monitor at least one and typically two available imaging resources during preview and acquisition phases of a measurement to quantify a decline in hydration, for example, and provide various related mitigation measures, as described herein.

A first one of such imaging resources includes any imaging system of an ocular aberrometry system that can be used to generate a Purkinje image of a known and repeatable structure reflected from a surface of an eye being examined. For example, eye tracker 130, a dedicated Purkinje imaging system (e.g., other modules 148), and/or other imaging system of ocular aberrometry systems 100 and/or 300 may be configured to generate and/or capture a first Purkinje reflection (P1) image of one or more LED reflections generated by LED array 132 reflecting from an outer surface of target 102 (e.g., an outer surface of a cornea of a human eye). In some embodiments, such first Purkinje reflection image of LED reflections can be processed by thresholding into a binary morphological representation providing for analysis of each reflected LED's pixel connectivity, for example, and/or an equivalent diameter and/or area. Such reflection characterization parameters can be quantified and monitored over a series of image or video frames to determine roughly in real time the imaged tear film hydration state.

A second one of such imaging resources includes wavefront sensor 120, which may be configured to generate wavefront sensor data associated with an eye being examined. As described herein, such wavefront sensor data may include an interferogram of fringe lines/pattern, and the Talbot Moiré fringe contrast associated with those interferograms typically degrades with the loss of hydration. Such tear film hydration degradation may be quantified within the Fourier transform domain of the interferogram. For example, the amplitude and shape of the neighborhood about the primary frequency peaks within the Fourier domain (e.g., spatial structure neighborhoods 723B-1, 723B-2 of FIG. 7B) may represent the derivative of the wavefront. Such neighborhoods may be directly affected as the tear film dehydrates, and the associated tear film hydration state can be quantified and monitored using various amplitude and size image analysis methods, as described herein.

In various embodiments, the focus and Talbot Moiré cameras (e.g., eye tracker 130 and wavefront sensor 120) may be synchronized; therefore, the image analysis of the separate image/video streams can coincide. For example, the amplitude of the Fourier peaks may be monitored along with the quality (e.g., the reflection characterization parameters) of the LED reflections to provide substantially real-time feedback to a doctor/technician as to the state of a tear film hydration state. For example, during an intraoperative or clinical exam, the instant tear film hydration state can be communicated to the clinician (e.g., through one or more display views). At the conclusion of an exam, a more comprehensive tear film hydration map and/or graph can be generated showing the evolution of relatively dry areas as a function of time.

Figure 9:
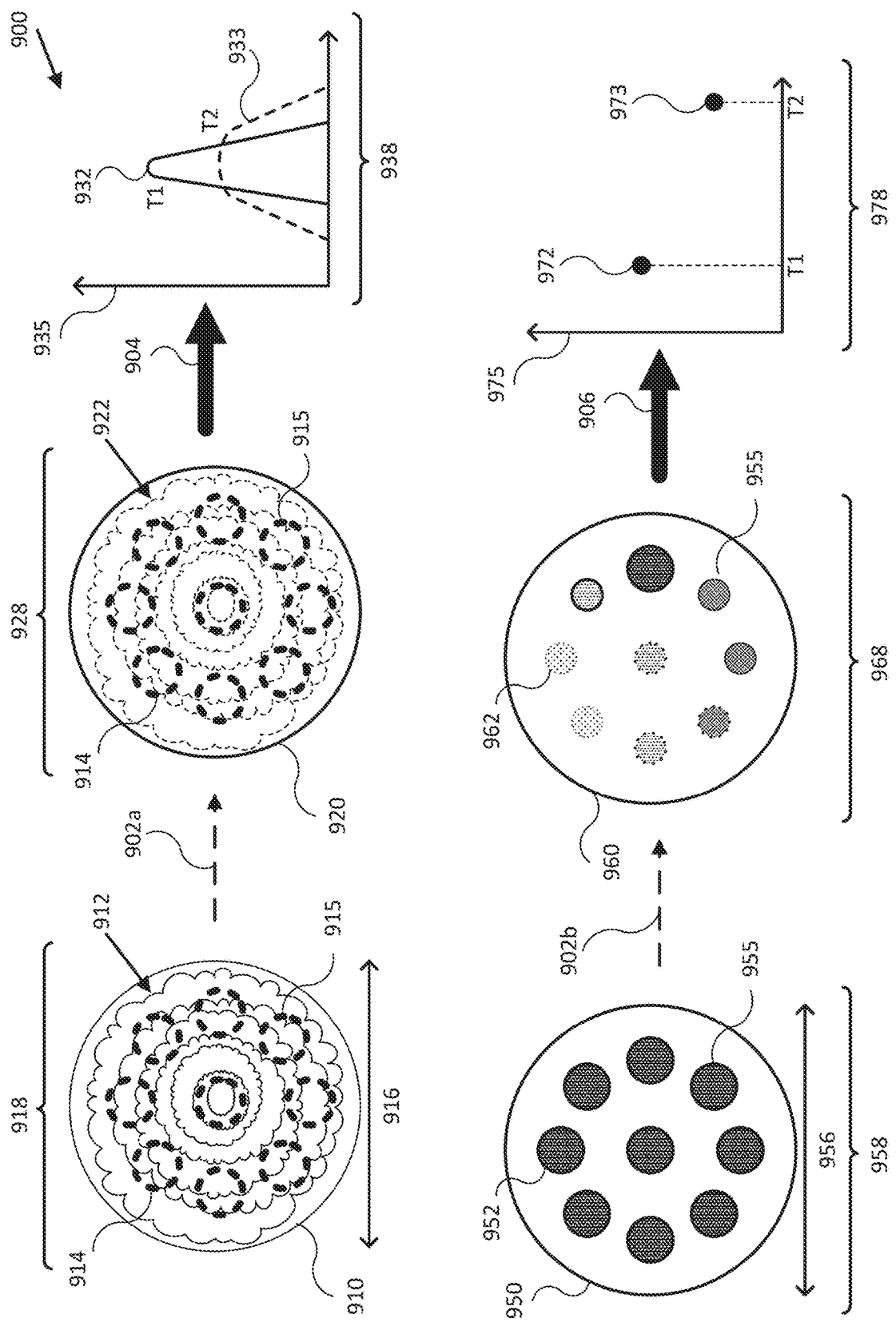
FIG. 9 illustrates a procedural diagram of a process to monitor tear film hydration for an ocular aberrometry system in accordance with an embodiment of the disclosure.

FIG. 9 illustrates a procedural diagram of a process 900 to monitor tear film hydration for an ocular aberrometry system in accordance with an embodiment of the disclosure. In the embodiment shown in FIG. 9, wavefront sensor data in the form of a first interferogram 910 of a human eye (e.g., including multiple roughly concentric fringe lines/pattern 912) may be acquired/captured at a first time T1, including wavefront sensor data associated with one or more monitoring areas 914, including specific monitoring area 915. In some embodiments, the shape, pattern, and/or distribution of monitoring areas 914 may roughly corresponding to the reflections of individual LEDs in LED array 132 from target 102, as described herein. In other embodiments, monitoring areas 914 may be selected to cover at least half or three quarters or all of the surface of target 102, and monitoring areas may or may not overlap each other. After a predetermined time period, wavefront sensor data in the form of a second interferogram 920 of the same eye may be acquired/captured at a second time T2, where fringe lines/pattern 922 of interferogram 920 has relatively degraded contrast compared to fringe lines/pattern 912 of interferogram 910. A Fourier transform of one or more of monitoring areas 914 may be determined (step 904) and plotted as graph 935, for example, to show the wavefront sensor data-based absolute and/or relative tear film hydration state of target 102.

For example, in one embodiment, graph 935 shows the Fourier transform of wavefront sensor data in the form of image data corresponding to monitoring area 915, where transform contour 932 corresponds to the Fourier transform of the image data captured at time T1, and where transform contour 933 corresponds to the Fourier transform of the image data captured at time T2. Various transform characteristics of the transform contours may be indicative of the absolute or relative tear film hydration state of target 102, such as the peak amplitudes, full width half maximums, areas, and/or other transform characteristics of transform contours 932, 933, each of which may be monitored and/or stored. In alternative embodiments, graph 935 may be a two-dimensional spatial plot, similar to that shown in display view 728B of FIG. 7B, for example, and the transform characteristics of the spatial peaks and corresponding spatial structure neighborhoods 723B-1, 723B-2 may be monitored and stored.

Over approximately the same time period, Purkinje image data in the form of a first Purkinje reflection (P1) image 950 of a human eye (e.g., including one or more reflections of known structure) may be acquired/captured at approximately first time T1, including Purkinje image data associated with one or more reflections 952 of LEDs of LED array 132 (e.g., including specific reflection 955). In some embodiments, the shape, pattern, and/or distribution of individual LEDs in LED array 132 may be selected to cover at least half or three quarters or all of the surface of target 102, and/or match monitoring areas 914, and such monitored structure reflections generally may not overlap each other. After a predetermined time period, Purkinje image data in the form of a second Purkinje (P1) image 960 of a human eye of the same eye may be acquired/captured at a second time T2, where reflections 962 of Purkinje (P1) image 960 have relatively poor pixel connectivity and/or are relatively small or indistinguishable from the background compared to reflections 952 of Purkinje (P1) image 950. Such reflection characterization parameters corresponding to each of reflections 952 and 962 (and/or averages, medians, and/or other statistical combinations and/or measures of the reflection characterization parameters) may be determined and plotted as graph 975, for example, to show the Purkinje image data-based absolute and/or relative tear film hydration state of target 102.

For example, in one embodiment, graph 975 shows the reflection characterization parameters of Purkinje image data corresponding to reflection/monitoring area 955, where reflection characterization parameter value 972 corresponds to the estimated diameter of reflection 955 as captured at time T1, and where reflection characterization parameter value 973 corresponds to the estimated diameter of reflection 955 as captured at time T2. Various reflection characterization parameters may be indicative of the absolute or relative tear film hydration state of target 102, such as the pixel connectivity, estimated diameter, estimated area, and/or other reflection characterization parameters of reflections 952, 962, each of which may be monitored and/or stored.

In various embodiments, interferograms 910, 920, Purkinje (P1) images 950, 960, and/or graphs 935, 975 may form at least part of a display view (e.g., display views 918, 928, 938, 958, 968, and/or 778) rendered on a display of user interface 146 and displayed to a user as user feedback with regard to the operation of ocular aberrometry systems 100 and/or 300, as shown. Moreover, process 900 of FIG. 9 may be used to generate a time series of images, graphs, tear film hydration states, and/or associated display views with more than two constituent images and/or states in the time series, including a stream of such images and/or states. In general operation, diameter 916 of interferogram 910 and diameter 956 of Purkinje (P1) image 950 may be configured to represent or correspond to roughly the diameter of the pupil of the examined eye.

Figure 10:
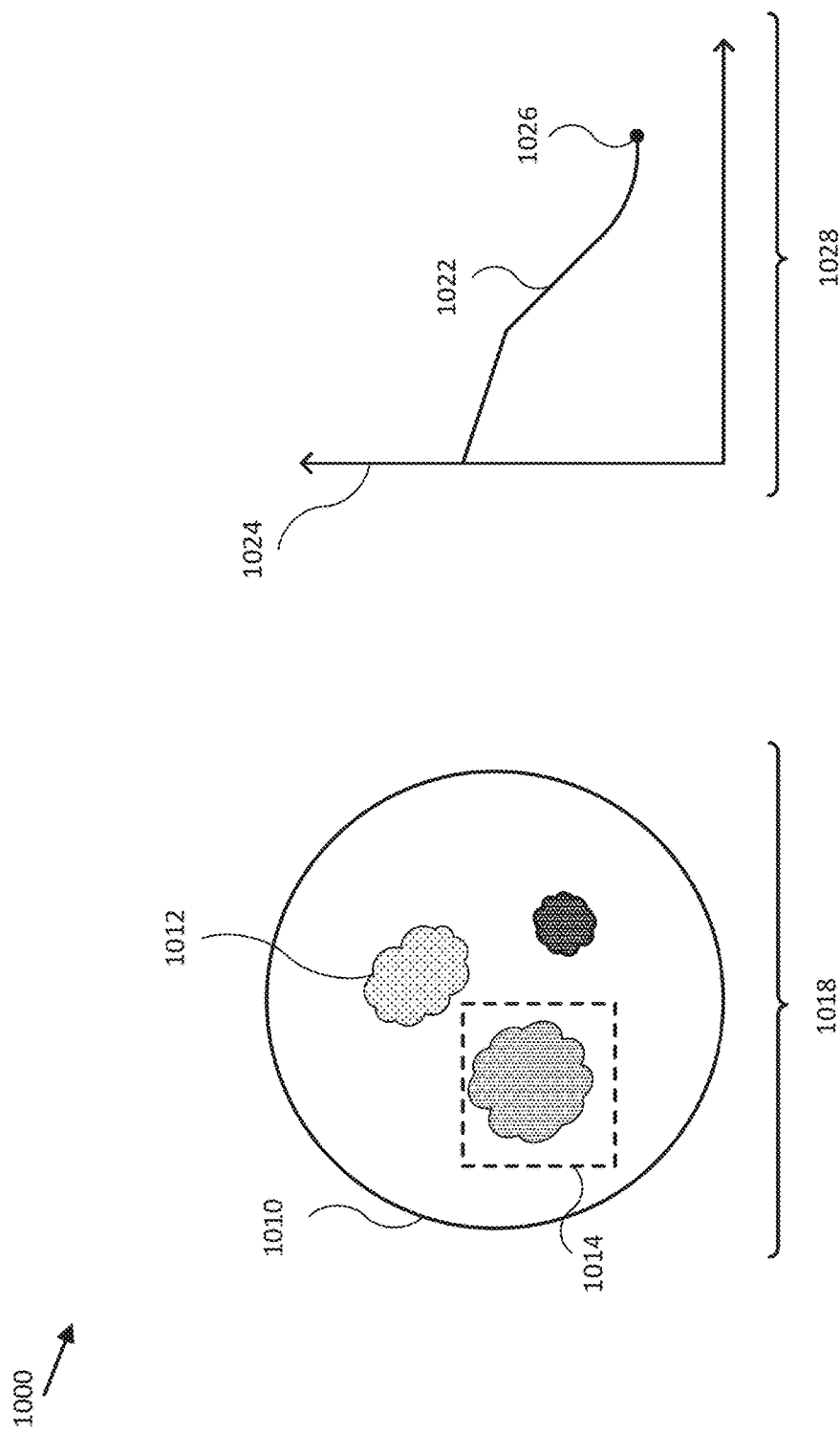
FIG. 10 illustrates a display view for monitoring tear film hydration for an ocular aberrometry system in accordance with an embodiment of the disclosure.

FIG. 10 illustrates a display view 100 (e.g., including one or more of display views 1018 and/or 1028) for monitoring tear film hydration for an ocular aberrometry system in accordance with an embodiment of the disclosure. In the embodiment shown in FIG. 10, display view 1018 includes tear film hydration map 1010 with one or more dehydrated portion indicators 1012. In some embodiments, tear film hydration map 1010 may be rendered according to a color palette and/or greyscale gradient configured to indicate the absolute and/or relative tear film hydration of an examined eye. For example, an absolute measure may be based on an ideal eye tear film hydration, such as a known tear film thickness typically present after a series of typical eye blinks. A relative measure may be based on an initial tear film hydration measured at the beginning of an exam (e.g., T1), for example, or when the patient indicates their eye feels properly hydrated, and all subsequent tear film hydration measurements may be determined relative to that initial measurement. In various embodiments, dehydrated portion indicators 1012 may be graphical overlays configured to identify portions of target 102 and/or tear film hydration map 1010 with tear film hydrations lower than an absolute measure, for example, or lower than expected after a particular time has passed (e.g., T2−T1), such as that based on an ideal eye model with typical dehydration rates.

Also shown in display view 1018 is selector box 1014. In some embodiments, user interface 146 may be configured to accept user input identifying the bounds of selector box 1014, for example, and ocular aberrometry system 100 may be configured to generate display view 1028 including hydration time evolution graph 1024 configured to illustrate a time evolution of the tear film hydration associated with the area of tear film hydration map 1010 bounded by selector box 1014. For example, in the embodiment shown in FIG. 10, hydration time evolution graph 1024 includes hydration evolution contour 1022 indicating the absolute or relative hydration of the portion of tear film hydration map 1010 bounded by selector box 1014, where point 1026 indicates the present time or the end of a particular exam series. In embodiments where selector box 1014 is absent, hydration time evolution graph 1024 may correspond to the average, mean, or other statistical measure of the entirety of tear film hydration map 1010. In various embodiments, selector box 1014 may be shaped differently, for example, or may correspond to selection of one or more of dehydrated portion indicators 1012, as described herein.

Figure 11:
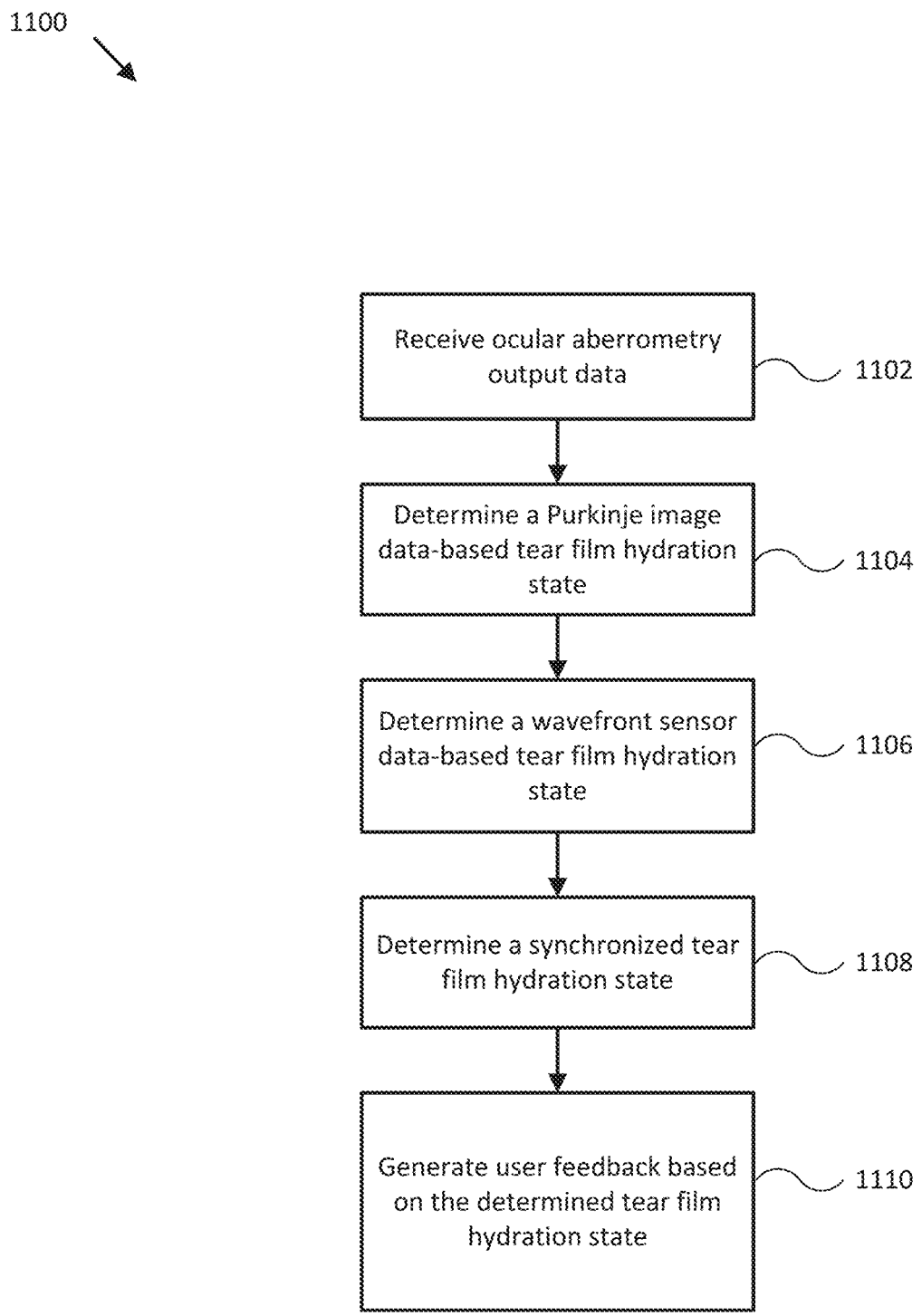
FIG. 11 illustrates a flow diagram of a process to operate an ocular aberrometry system in accordance with an embodiment of the disclosure.

FIG. 11 illustrates a flow diagram of a process 1100 to operate an ocular aberrometry systems 100 and/or 300 with tear film hydration monitoring in accordance with an embodiment of the disclosure. It should be appreciated that any step, sub-step, sub-process, or block of process 1100 may be performed in an order or arrangement different from the embodiments illustrated by FIG. 11. For example, in other embodiments, one or more blocks may be omitted from or added to the process. Furthermore, block inputs, block outputs, various sensor signals, sensor information, calibration parameters, and/or other operational parameters may be stored to one or more memories prior to moving to a following portion of a corresponding process. Although process 1100 is described with reference to systems, processes, control loops, and images described in reference to FIGS. 1-10, process 1100 may be performed by other systems different from those systems, processes, control loops, and images and including a different selection of electronic devices, sensors, assemblies, mobile structures, and/or mobile structure attributes, for example.

In block 1102, ocular aberrometry output is received. For example, controller 140, server 150, and/or distributed server system 154 may be configured to receive ocular aberrometry output data including at least wavefront sensor data provided by wavefront sensor 120 and/or Purkinje image data provided by an imaging system of ocular aberrometry system 100 (e.g., eye tracker 130, other modules 148. More generally, the ocular aberrometry output data may include any one or more of wavefront sensor data provided by wavefront sensor 120, OCT sensor data provided by OCT sensor 122, eye tracker data provided by eye tracker 130, and/or other output data provided by ocular aberrometry system 100, as described herein. Wavefront sensor data provided by wavefront sensor 120 may include interferogram 910 of an examined eye, for example, and Purkinje image data provided by an imaging system of ocular aberrometry system 100 may include first Purkinje reflection (P1) image 950 of the examined eye, for example.

In block 1104, a Purkinje image data-based tear film hydration state is determined. For example, controller 140, server 150, and/or distributed server system 154 may be configured to determine a tear film hydration state corresponding to target 102 based, at least in part, on Purkinje image data received in block 1102. In some embodiments controller 140, server 150, and/or distributed server system 154 may be configured to determine the tear film hydration state by determining a threshold-based binary first Purkinje reflection (P1) image (e.g., a binary morphological representation of the P1 image, where reflection pixels=1 and non-reflection pixels=0) based, at least in part, on a captured P1 image 950, and then determining one or more reflection characterization parameters (e.g., reflection pixel connectivity, estimated diameter, estimated area) corresponding to a tear film hydration state of target 102 based, at least in part, on the threshold-based binary P1 image. Determining such threshold-based binary P1 image may include determining, for each pixel of P1 image 950, a pixel intensity or luminosity for the pixel, assigning a pixel value of one for pixels with intensities or luminosities equal to or above a threshold intensity or luminosity, and assigning a pixel value of zero for pixels with intensities or luminosities below the threshold intensity or luminosity. In some embodiments, the threshold may be predetermined (e.g., by user selection), for example, or may be adaptive (e.g., based on an average, median, or other statistical measure of intensities and/or luminosities of pixel in P1 image 950.

In block 1106, a wavefront sensor data-based tear film hydration state is determined. For example, controller 140, server 150, and/or distributed server system 154 may be configured to determine a tear film hydration state corresponding to target 102 based, at least in part, on wavefront sensor data received in block 1102. In some embodiments controller 140, server 150, and/or distributed server system 154 may be configured to determine the tear film hydration state by determining a Fourier transform of wavefront sensor data associated with a monitoring area of the wavefront sensor data and determining one or more transform characteristics based, at least in part, on the Fourier transform of wavefront sensor data. In various embodiments, the transform characteristics may include one or more fringe contrast metrics, for example, such as peak amplitudes, neighborhood diameters and/or areas, and/or one or more contour characteristics, such as peak amplitudes, full width half maximums, areas, and/or other characteristics of transform contours, as described herein.

In block 1108, a synchronized tear film hydration state is determined. For example, controller 140, server 150, and/or distributed server system 154 may be configured to determine a synchronized tear film hydration state corresponding to target 102 based, at least in part, on the tear film hydration states determined in blocks 1104 and 1106. In some embodiments controller 140, server 150, and/or distributed server system 154 may be configured to determine the synchronized tear film hydration state by controlling wavefront sensor 120 and eye tracker 130 (e.g., or another imaging sensor of system 100) to image target 102 at approximately the same times (e.g., T1, T2) and/or according to approximately the same rates (e.g., captures/second). In various embodiments, controller 140, server 150, and/or distributed server system 154 may be configured to determine a synchronized tear film hydration state by combining a Purkinje image data-based tear film hydration state with a wavefront sensor data-based tear film hydration state by determining the average, median, and/or other statistical combination of the Purkinje image data-based tear film hydration states with the wavefront sensor data-based tear film hydration states.

In block 1110, user feedback is generated. For example, controller 140, server 150, and/or distributed server system 154 may be configured to generate user feedback corresponding to the tear film hydration state determined in blocks 1104, 1106, and/or 1108, based, at least in part, on any one or combination of the determined tear film hydration states and/or ocular aberrometry output data received in block 1102, such as a display view of interferogram 910, first Purkinje reflection (P1) image 950, and/or a graph or map of a time evolution or series of determined tear film hydration states, such as a display view of tear film hydration map 1010 and/or tear film hydration graph 1024. In various embodiments, controller 140, server 150, and/or distributed server system 154 may be configured to generate user feedback using any of the processes described herein with respect to FIGS. 4-8.

In additional embodiments, controller 140, server 150, and/or distributed server system 154 may be configured to perform various operations based, at least in part, on the tear film hydration states determined in blocks 1104, 1106, and/or 1008, for example, and/or on or in combination with the user feedback generated in block 1110. For example, controller 140, server 150, and/or distributed server system 154 may be configured to detect that one or more of the tear film hydration states determined in blocks 1104, 1106, and/or 1008, dehydrated portion indicators 1012, tear film hydration map 1010, and/or hydration time evolution graph 1024 indicate a tear film hydration level below a minimum aberrometry hydration threshold, for example, and omit wavefront sensor data and/or aberrometry measurements of an exam series that are associated with tear film hydration levels below the minimum aberrometry hydration threshold. In other embodiments, aberrometry systems 100 and/or 300 may be configured to prompt (e.g., through visible or audible user feedback) a patient to blink or an operator to provide saline when any portion of target 102 is detected as below the minimum aberrometry hydration threshold, for example, or when a preset percentage (e.g., 10%) of target 102 is detected as below the minimum aberrometry hydration threshold. In further embodiments, aberrometry systems 100 and/or 300 may be configured to project air (e.g., to cause a patient to blink) or saline (to wet target 102) onto target 102 when any portion of target 102, or when a preset percentage of target 102, is detected as below the minimum aberrometry hydration threshold.

Embodiments of the present disclosure can thus provide substantially real time (e.g., 30 frames/second) user feedback (e.g., display views including various graphics) and reliable and accurate monitoring of ocular aberrations, and/or other characteristics of optical target 102 affecting characterization of such ocular aberrations, as described herein. Such embodiments may be used to assist in a variety of types of clinical and intraoperative eye exams and help provide improved surgical results.

Where applicable, various embodiments provided by the present disclosure can be implemented using hardware, software, or combinations of hardware and software. Also, where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:

1. An ocular aberrometry system comprising: a wavefront sensor configured to provide wavefront sensor data associated with an optical target monitored by the ocular aberrometry system; and a logic device configured to communicate with the wavefront sensor, wherein the logic device is configured to: receive ocular aberrometry output data comprising at least the wavefront sensor data provided by the wavefront sensor; and determine a tear film hydration state associated with the optical target based, at least in part, on the received ocular aberrometry output data; determine when a portion of the optical target or when a preset percentage of optical target is detected as below a predetermined minimum aberrometry hydration threshold; and a projection device to project saline onto the optical target when the portion of the optical target or when the preset percentage of optical target is detected as below the predetermined minimum aberrometry hydration threshold.

2. The ocular aberrometry system of claim 1, wherein the tear film hydration state comprises a wavefront sensor data-based tear film hydration state, and wherein the determining the tear film hydration state comprises:

determining a Fourier transform of the received wavefront sensor data; and
determining the wavefront sensor data-based tear film hydration state based, at least in part, on one or more transform characteristics corresponding to the determined Fourier transform of the received wavefront sensor data, wherein the one or more transform characteristics comprises at least one of a peak amplitude, a full width half maximum, an area, a spatial peak amplitude, and/or a spatial structure neighborhood area.

3. The ocular aberrometry system of claim 1, wherein the ocular aberrometry output data comprises Purkinje image data provided by an imaging system of the ocular aberrometry system, the tear film hydration state comprises a Purkinje image data-based tear film hydration state, and the determining the tear film hydration state comprises:
  determining a threshold-based binary first Purkinje reflection (P1) image based, at least in part, on the received Purkinje image data; and
  determining one or more reflection characterization parameters based, at least in part, on the threshold-based binary P1 image.

4. The ocular aberrometry system of claim 3, further comprising the imaging system of the ocular aberrometry system, wherein:
  the imaging system comprises an eye tracker; and
  the one or more reflection characterization parameters comprises at least one of a pixel connectivity, an estimated diameter, and/or an estimated area of at least one reflection in the received Purkinje image data.

5. The ocular aberrometry system of claim 1, wherein the tear film hydration state comprises a synchronized tear film hydration state, and wherein the determining the tear film hydration state comprises:
  controlling the wavefront sensor and an imaging sensor of the ocular aberrometry system to image the optical target at approximately a same time and/or according to a same rate; and
  combining a Purkinje image data-based tear film hydration state determined based, at least in part, on Purkinje image data provided by the imaging system, with a wavefront sensor data-based tear film hydration state determine based, at least in part, on the received wavefront sensor data, by determining the average, median, and/or other statistical combination of the Purkinje image data-based tear film hydration state with the wavefront sensor data-based tear film hydration state.

6. The ocular aberrometry system of claim 5, wherein:
  the received Purkinje image data comprises one or more reflections corresponding to light emitting diodes (LEDs) in an LED array configured to illuminate the optical target.

7. The ocular aberrometry system of claim 1, further comprising:
  a display device, and
  wherein the logic device is configured generate, on the display device, user feedback corresponding to the determined tear film hydration state based, at least in part, on the received aberrometry output data and/or the determined tear film hydration state.

8. The ocular aberrometry system of claim 7, wherein the generating the user feedback corresponding to the determined tear film hydration state comprises:
  generating a display view comprising a tear film hydration map corresponding to the determined tear film hydration status and comprising at least one dehydrated portion indicator and/or a hydration time evolution graph comprising at least one hydration evolution contour.

9. The ocular aberrometry system of claim 8, wherein the logic device is configured to:
  receive user input selecting bounds for a selector box indicating a selected area of the tear film hydration map, wherein the at least one hydration evolution contour corresponds to a time evolution of tear film hydration associated with the selected area of the tear film hydration map.

10. The ocular aberrometry system of claim 1, wherein the logic device is configured to:
  detect that the determined tear film hydration state indicates a tear film hydration level below a minimum aberrometry hydration threshold; and
  omit wavefront sensor data of the received wavefront sensor data that is associated with the detected tear film hydration level below the minimum aberrometry hydration threshold.

11. The ocular aberrometry system of claim 1, wherein the logic device is configured to:
  detect that the determined tear film hydration state indicates a tear film hydration level below a minimum aberrometry hydration threshold; and
  prompt a patient of the ocular aberrometry system to blink.

12. A method comprising:
  receiving ocular aberrometry output data from an ocular aberrometry system comprising a wavefront sensor, wherein the ocular aberrometry output data comprises at least wavefront sensor data associated with an optical target monitored by the ocular aberrometry system;
  determining a tear film hydration state associated with the optical target based, at least in part, on the received ocular aberrometry output data; and
  determining when a portion of the optical target or when a preset percentage of optical target is detected as below a predetermined minimum aberrometry hydration threshold; and
  projecting, from a projection device, saline onto the optical target when the portion of the optical target or when the preset percentage of optical target is detected as below the predetermined minimum aberrometry hydration threshold.

13. The method of claim 12, wherein the tear film hydration state comprises a wavefront sensor data-based tear film hydration state, and wherein the determining the tear film hydration state comprises:
  determining a Fourier transform of the received wavefront sensor data; and
  determining the wavefront sensor data-based tear film hydration state based, at least in part, on one or more transform characteristics corresponding to the determined Fourier transform of the received wavefront sensor data, wherein the one or more transform characteristics comprises at least one of a peak amplitude, a full width half maximum, an area, a spatial peak amplitude, and/or a spatial structure neighborhood area.

14. The method of claim 12, wherein the ocular aberrometry output data comprises Purkinje image data provided by an imaging system of the ocular aberrometry system, the tear film hydration state comprises a Purkinje image data-based tear film hydration state, and the determining the tear film hydration state comprises:
  determining a threshold-based binary first Purkinje reflection (P1) image based, at least in part, on the received Purkinje image data; and determining one or more reflection characterization parameters based, at least in part, on the threshold-based binary P1 image.

15. The method of claim 14, further comprising the imaging system of the ocular aberrometry system, wherein:
the imaging system comprises an eye tracker; and
the one or more reflection characterization parameters comprises at least one of a pixel connectivity, an estimated diameter, and/or an estimated area of at least one reflection in the received Purkinje image data.

16. The method of claim 12, wherein the tear film hydration state comprises a synchronized tear film hydration state, and wherein the determining the tear film hydration state comprises:
controlling the wavefront sensor and an imaging sensor of the ocular aberrometry system to image the optical target at approximately a same time and/or according to a same rate; and
combining a Purkinje image data-based tear film hydration state determined based, at least in part, on Purkinje image data provided by the imaging system, with a wavefront sensor data-based tear film hydration state determine based, at least in part, on the received wavefront sensor data, by determining the average, median, and/or other statistical combination of the Purkinje image data-based tear film hydration state with the wavefront sensor data-based tear film hydration state.

17. The method of claim 16, wherein:
the received Purkinje image data comprises one or more reflections corresponding to light emitting diodes (LEDs) in an LED array configured to illuminate the optical target.

18. The method of claim 12, further comprising:
generating, on a display device, user feedback corresponding to the determined tear film hydration state based, at least in part, on the received aberrometry output data and/or the determined tear film hydration state.

19. The method of claim 18, wherein the generating the user feedback corresponding to the determined tear film hydration state comprises:
generating a display view comprising a tear film hydration map corresponding to the determined tear film hydration status and comprising at least one dehydrated portion indicator and/or a hydration time evolution graph comprising at least one hydration evolution contour.

20. The method of claim 19, further comprising:
receiving user input selecting bounds for a selector box indicating a selected area of the tear film hydration map, wherein the at least one hydration evolution contour corresponds to a time evolution of tear film hydration associated with the selected area of the tear film hydration map.

21. The method of claim 12, further comprising:
detecting that the determined tear film hydration state indicates a tear film hydration level below a minimum aberrometry hydration threshold; and
omitting wavefront sensor data of the received wavefront sensor data that is associated with the detected tear film hydration level below the minimum aberrometry hydration threshold.

22. The method of claim 12, further comprising:
detecting that the determined tear film hydration state indicates a tear film hydration level below a minimum aberrometry hydration threshold; and
prompting a patient of the ocular aberrometry system to blink.

* * * * *